US008475387B2

(12) United States Patent
Derchak et al.

(10) Patent No.: US 8,475,387 B2
(45) Date of Patent: Jul. 2, 2013

(54) AUTOMATIC AND AMBULATORY MONITORING OF CONGESTIVE HEART FAILURE PATIENTS

(75) Inventors: P. Alexander Derchak, Ventura, CA (US); Gary Michael Lucia, Ventura, CA (US); Lance Jonathan Myers, Ventura, CA (US)

(73) Assignee: adidas AG, Herzogenaurach (DE)

( * ) Notice: Subject to any disclaimer, the term of this patent is extended or adjusted under 35 U.S.C. 154(b) by 1145 days.

(21) Appl. No.: 11/764,527

(22) Filed: Jun. 18, 2007

(65) Prior Publication Data

US 2008/0045815 A1    Feb. 21, 2008

Related U.S. Application Data

(60) Provisional application No. 60/815,367, filed on Jun. 20, 2006.

(51) Int. Cl.
*A61B 5/08* (2006.01)

(52) U.S. Cl.
USPC ............... 600/529; 600/301; 600/534; 607/6

(58) Field of Classification Search
USPC ............. 607/6; 600/301, 309–310, 322–324, 600/529, 534
See application file for complete search history.

(56) References Cited

U.S. PATENT DOCUMENTS

| 3,534,727 | A | 10/1970 | Roman |
| 3,731,184 | A | 5/1973 | Goldberg et al. |
| 3,874,368 | A | 4/1975 | Asrican |
| 3,926,177 | A | 12/1975 | Hardway, Jr. et al. |
| 4,016,868 | A | 4/1977 | Allison ...................... 128/2.1 E |
| 4,033,332 | A | 7/1977 | Hardway, Jr. et al. |
| 4,102,331 | A | 7/1978 | Grayzel et al. |
| 4,258,718 | A | 3/1981 | Goldman |
| 4,267,845 | A | 5/1981 | Robertson, Jr. et al. |
| 4,289,142 | A | 9/1981 | Kearns |
| 4,306,567 | A | 12/1981 | Krasner ........................ 128/671 |
| 4,308,872 | A | 1/1982 | Watson et al. ................. 128/725 |

(Continued)

FOREIGN PATENT DOCUMENTS

| DE | 4214263 A | 11/1993 |
| EP | 0262778 | 4/1988 |

(Continued)

OTHER PUBLICATIONS

Costa et al., Multiscale Entropy Analysis of Complex Physiologic Time Series, Physical Review Letters, vol. 89, No. 6 (Aug. 5, 2002) pp. 1-4.*

(Continued)

*Primary Examiner* — Rex R Holmes
(74) *Attorney, Agent, or Firm* — Sterne, Kessler, Goldstein & Fox PLLC

(57) ABSTRACT

This invention provides methods for non-invasively monitoring patients with congestive heart failure (CHF) and for reporting and/or warning of changes in the patients' status. The methods gather physiological data and combine the data into parameters by which the severity of CHF can be judged. Preferred parameters include periodic breathing and heart rate variability. This invention also provides systems for carrying out these methods which permit patients to engage in their normal daily activities. Preferably, physiological data analysis is performed by a portable electronic unit carried by the patients.

16 Claims, 8 Drawing Sheets

U.S. PATENT DOCUMENTS

| | | | | |
|---|---|---|---|---|
| 4,373,534 A | 2/1983 | Watson | | 128/725 |
| 4,387,722 A | 6/1983 | Kearns | | |
| 4,433,693 A | 2/1984 | Hochstein | | 128/721 |
| 4,446,872 A | 5/1984 | Marsoner et al. | | |
| 4,452,252 A | 6/1984 | Sackner | | 128/671 |
| 4,456,015 A | 6/1984 | Sackner | | 128/721 |
| 4,463,764 A | 8/1984 | Anderson et al. | | 128/719 |
| 4,494,553 A | 1/1985 | Sciarra et al. | | |
| 4,537,196 A | 8/1985 | Phillipps et al. | | |
| 4,545,376 A | 10/1985 | Beiter | | |
| 4,546,777 A | 10/1985 | Groch et al. | | |
| 4,548,204 A | 10/1985 | Groch et al. | | |
| 4,549,552 A | 10/1985 | Groch et al. | | |
| 4,572,197 A | 2/1986 | Moore et al. | | |
| 4,580,572 A | 4/1986 | Granek et al. | | |
| 4,648,407 A | 3/1987 | Sackner | | 128/721 |
| 4,672,975 A | 6/1987 | Sirota | | |
| 4,753,988 A | 6/1988 | Henton et al. | | 525/73 |
| 4,777,962 A | 10/1988 | Watson et al. | | 128/716 |
| 4,796,639 A | 1/1989 | Snow et al. | | 128/719 |
| 4,800,495 A | 1/1989 | Smith | | 364/413.03 |
| 4,807,640 A | 2/1989 | Watson et al. | | 128/721 |
| 4,815,473 A | 3/1989 | Watson et al. | | 128/721 |
| 4,817,625 A | 4/1989 | Miles | | 128/721 |
| 4,819,752 A | 4/1989 | Zelin | | |
| 4,834,109 A | 5/1989 | Watson | | 128/721 |
| 4,860,766 A | 8/1989 | Sackner | | 128/748 |
| 4,863,265 A | 9/1989 | Flower et al. | | |
| 4,867,571 A | 9/1989 | Frick et al. | | |
| 4,889,131 A | 12/1989 | Salem et al. | | |
| 4,909,260 A | 3/1990 | Salem et al. | | |
| 4,911,167 A | 3/1990 | Corenman et al. | | |
| 4,920,969 A | 5/1990 | Suzuki et al. | | |
| 4,928,692 A | 5/1990 | Goodman et al. | | |
| 4,934,372 A | 6/1990 | Corenman et al. | | |
| 4,955,379 A | 9/1990 | Hall | | |
| 4,960,118 A | 10/1990 | Pennock | | 128/200.4 |
| 4,966,155 A | 10/1990 | Jackson | | 128/671 |
| 4,972,842 A | 11/1990 | Korten et al. | | 128/716 |
| 4,981,139 A | 1/1991 | Pfohl | | |
| 4,986,277 A | 1/1991 | Sackner | | 128/672 |
| 5,007,427 A | 4/1991 | Suzuki et al. | | 128/659 |
| 5,025,791 A | 6/1991 | Niwa | | |
| 5,036,857 A | 8/1991 | Semmlow et al. | | |
| 5,040,540 A | 8/1991 | Sackner | | 128/672 |
| 5,074,129 A | 12/1991 | Matthew | | 66/192 |
| 5,076,801 A | 12/1991 | Schroll | | |
| 5,099,841 A | 3/1992 | Heinonen et al. | | |
| 5,099,855 A | 3/1992 | Yount | | |
| 5,111,817 A | 5/1992 | Clark et al. | | |
| 5,131,399 A | 7/1992 | Sciarra | | 128/671 |
| 5,143,089 A | 9/1992 | Alt | | |
| 5,159,935 A | 11/1992 | Sackner et al. | | 128/721 |
| 5,173,151 A | 12/1992 | Namose | | |
| 5,178,151 A | 1/1993 | Sackner | | 128/672 |
| 5,224,479 A | 7/1993 | Sekine | | |
| 5,241,300 A | 8/1993 | Buschmann | | |
| 5,271,551 A | 12/1993 | Roepke | | |
| 5,295,490 A | 3/1994 | Dodakian | | |
| 5,299,120 A | 3/1994 | Kaestle | | |
| 5,301,678 A | 4/1994 | Watson et al. | | 128/721 |
| 5,329,932 A | 7/1994 | Yount | | |
| 5,331,968 A | 7/1994 | Williams et al. | | 128/721 |
| 5,333,106 A | 7/1994 | Lanpher et al. | | |
| 5,348,008 A | 9/1994 | Bornn et al. | | 128/642 |
| 5,353,793 A | 10/1994 | Bornn et al. | | 128/642 |
| 5,416,961 A | 5/1995 | Vinay | | 128/165 |
| 5,447,164 A | 9/1995 | Shaya et al. | | 128/710 |
| RE35,122 E | 12/1995 | Corenman et al. | | 600/633 |
| 5,520,192 A | 5/1996 | Kitney et al. | | |
| 5,533,511 A | 7/1996 | Kaspari et al. | | 128/672 |
| 5,535,738 A | 7/1996 | Estes et al. | | |
| 5,544,661 A | 8/1996 | Davis et al. | | 128/700 |
| 5,564,429 A | 10/1996 | Bornn et al. | | 128/696 |
| 5,577,510 A | 11/1996 | Chittum et al. | | 128/709 |
| 5,582,337 A | 12/1996 | McPherson et al. | | |
| 5,584,295 A | 12/1996 | Muller et al. | | |
| 5,588,425 A | 12/1996 | Sackner et al. | | 128/632 |
| 5,601,088 A | 2/1997 | Swanson et al. | | 128/697 |
| 5,611,085 A | 3/1997 | Rasmussen | | |
| 5,617,847 A | 4/1997 | Howe | | |
| 5,694,939 A | 12/1997 | Cowings | | 128/671 |
| 5,718,234 A | 2/1998 | Warden et al. | | |
| 5,719,950 A | 2/1998 | Osten et al. | | |
| 5,720,709 A | 2/1998 | Schnall | | |
| 5,724,025 A | 3/1998 | Tavori | | |
| 5,749,365 A | 5/1998 | Magill | | 128/671 |
| 5,820,567 A | 10/1998 | Mackie | | 600/519 |
| 5,825,293 A | 10/1998 | Ahmed | | |
| 5,848,027 A | 12/1998 | Dotter | | |
| 5,882,307 A | 3/1999 | Wright et al. | | |
| 5,899,855 A | 5/1999 | Brown | | 600/301 |
| 5,913,830 A | 6/1999 | Miles | | 600/535 |
| 5,921,920 A | 7/1999 | Marshall et al. | | |
| 5,937,854 A | 8/1999 | Stenzler | | |
| 5,989,193 A | 11/1999 | Sullivan | | |
| 5,991,922 A | 11/1999 | Banks | | 2/69 |
| 6,002,952 A | 12/1999 | Diab et al. | | |
| 6,015,388 A | 1/2000 | Sackner et al. | | 600/529 |
| 6,018,677 A | 1/2000 | Vidrine et al. | | |
| 6,035,154 A | 3/2000 | Takahata et al. | | |
| 6,047,203 A | 4/2000 | Sackner et al. | | 600/388 |
| 6,066,093 A | 5/2000 | Kelly et al. | | 600/386 |
| 6,067,462 A | 5/2000 | Diab et al. | | 600/310 |
| 6,068,568 A | 5/2000 | Kozakura et al. | | 474/212 |
| 6,070,098 A | 5/2000 | Moore-Ede et al. | | 600/544 |
| 6,120,441 A | 9/2000 | Griebel | | |
| 6,142,953 A | 11/2000 | Burton et al. | | 600/534 |
| 6,145,551 A | 11/2000 | Jayaraman et al. | | |
| 6,179,786 B1 | 1/2001 | Young | | |
| 6,198,394 B1 | 3/2001 | Jacobsen et al. | | |
| 6,223,072 B1 | 4/2001 | Mika et al. | | 600/510 |
| 6,254,552 B1 | 7/2001 | Lewis et al. | | 600/603 |
| 6,261,238 B1 | 7/2001 | Gavriely | | 600/532 |
| 6,273,859 B1 | 8/2001 | Remmers et al. | | |
| 6,287,264 B1 | 9/2001 | Hoffman | | |
| 6,302,844 B1 | 10/2001 | Walker et al. | | 600/300 |
| 6,306,088 B1 | 10/2001 | Krausman et al. | | |
| 6,341,504 B1 | 1/2002 | Istook | | 66/172 E |
| 6,361,501 B1 | 3/2002 | Amano et al. | | |
| 6,381,482 B1 | 4/2002 | Jayaraman et al. | | |
| 6,413,225 B1 | 7/2002 | Sackner et al. | | 600/529 |
| 6,419,636 B1 | 7/2002 | Young et al. | | |
| 6,436,057 B1 | 8/2002 | Goldsmith et al. | | 600/586 |
| 6,443,890 B1 | 9/2002 | Schulze et al. | | |
| 6,449,504 B1 | 9/2002 | Conley et al. | | 600/523 |
| 6,454,719 B1 | 9/2002 | Greenhut | | 600/484 |
| 6,461,307 B1 | 10/2002 | Kristbjarnarson et al. | | |
| 6,463,385 B1 | 10/2002 | Fry | | |
| 6,478,736 B1 | 11/2002 | Mault | | |
| 6,483,929 B1 | 11/2002 | Murakami et al. | | |
| 6,485,431 B1 | 11/2002 | Campbell | | |
| 6,506,153 B1 | 1/2003 | Littek et al. | | |
| 6,511,424 B1 | 1/2003 | Moore-Ede et al. | | 600/300 |
| 6,513,532 B2 | 2/2003 | Mault et al. | | |
| 6,551,252 B2 | 4/2003 | Sackner et al. | | 600/536 |
| 6,579,231 B1 | 6/2003 | Phipps | | 600/300 |
| 6,589,188 B1 * | 7/2003 | Street et al. | | 600/538 |
| 6,604,115 B1 | 8/2003 | Gary, Jr. et al. | | 707/104.1 |
| 6,633,772 B2 | 10/2003 | Ford et al. | | 600/345 |
| 6,647,252 B2 | 11/2003 | Smith et al. | | |
| 6,656,127 B1 | 12/2003 | Ben-Oren et al. | | 600/532 |
| 6,687,523 B1 | 2/2004 | Jayaramen et al. | | |
| 6,699,194 B1 | 3/2004 | Diab et al. | | |
| 6,702,752 B2 | 3/2004 | Dekker | | |
| 6,709,402 B2 | 3/2004 | Dekker | | |
| 6,721,594 B2 | 4/2004 | Conley et al. | | 600/523 |
| 6,723,055 B2 | 4/2004 | Hoffman | | 600/538 |
| 6,726,636 B2 | 4/2004 | Der Ghazarian et al. | | |
| 6,727,197 B1 | 4/2004 | Wilson et al. | | 442/301 |
| 6,747,561 B1 | 6/2004 | Reeves | | |
| 6,775,389 B2 | 8/2004 | Harrison et al. | | |
| 6,783,498 B2 | 8/2004 | Sackner et al. | | 600/481 |
| 6,801,916 B2 | 10/2004 | Roberge et al. | | 707/101 |
| 6,817,979 B2 | 11/2004 | Nihtila | | |
| 6,858,006 B2 * | 2/2005 | MacCarter et al. | | 600/300 |
| 6,881,192 B1 | 4/2005 | Park | | 600/529 |

| | | |
|---|---|---|
| 6,941,775 B2 | 9/2005 | Sharma |
| 6,961,448 B2 | 11/2005 | Nichols et al. |
| 6,970,731 B1 | 11/2005 | Jayaraman et al. |
| 6,993,378 B2 | 1/2006 | Wiederhold et al. |
| 7,001,337 B2 | 2/2006 | Dekker |
| 7,073,129 B1 | 7/2006 | Robarts et al. |
| 7,077,810 B2 | 7/2006 | Lange et al. |
| 7,081,095 B2 | 7/2006 | Lynn et al. ............ 600/538 |
| 7,082,327 B2 | 7/2006 | Houben |
| 7,099,714 B2 | 8/2006 | Houben |
| 7,104,962 B2 | 9/2006 | Lomask et al. ........ 600/529 |
| 7,154,398 B2 | 12/2006 | Chen et al. |
| 7,207,948 B2 | 4/2007 | Coyle |
| 7,254,516 B2 | 8/2007 | Case, Jr. et al. |
| 7,267,652 B2 | 9/2007 | Coyle et al. |
| 7,319,385 B2 | 1/2008 | Ruha |
| 7,559,902 B2 | 7/2009 | Ting et al. |
| 7,604,603 B2 | 10/2009 | Sackner et al. |
| 7,670,295 B2 | 3/2010 | Sackner et al. |
| 7,727,161 B2 | 6/2010 | Coyle et al. |
| 7,762,953 B2 | 7/2010 | Derchak et al. |
| 7,809,433 B2 | 10/2010 | Keenan |
| 7,878,979 B2 | 2/2011 | Derchak |
| 7,896,813 B2 * | 3/2011 | Sowelam et al. ........ 600/529 |
| 2002/0032386 A1 | 3/2002 | Sackner et al. |
| 2002/0084130 A1 | 7/2002 | Der Ghazarian et al. |
| 2002/0090667 A1 | 7/2002 | Ratcliffe et al. |
| 2002/0123701 A1 | 9/2002 | Eriksen |
| 2003/0100843 A1 | 5/2003 | Hoffman |
| 2003/0135097 A1 | 7/2003 | Wiederhold et al. |
| 2003/0135127 A1 | 7/2003 | Sackner et al. ........ 600/536 |
| 2003/0185408 A1 | 10/2003 | Causevic et al. |
| 2003/0187341 A1 | 10/2003 | Sackner et al. |
| 2004/0010420 A1 | 1/2004 | Rooks |
| 2004/0019289 A1 | 1/2004 | Ross |
| 2004/0030224 A1 | 2/2004 | Sotos et al. |
| 2004/0111040 A1 | 6/2004 | Ni et al. ............... 600/534 |
| 2004/0116784 A1 | 6/2004 | Gavish |
| 2004/0117204 A1 | 6/2004 | Mazar |
| 2004/0122334 A1 | 6/2004 | Yamashiro |
| 2004/0143194 A1 | 7/2004 | Kihara et al. ......... 600/534 |
| 2004/0204636 A1 | 10/2004 | Diab et al. |
| 2004/0210147 A1 | 10/2004 | Houben |
| 2004/0225227 A1 | 11/2004 | Newman |
| 2004/0249299 A1 | 12/2004 | Cobb ..................... 600/529 |
| 2005/0027207 A1 | 2/2005 | Westbrook et al. |
| 2005/0054941 A1 | 3/2005 | Ting et al. ............ 600/529 |
| 2005/0076908 A1 | 4/2005 | Lee et al. ........... 128/204.23 |
| 2005/0119586 A1 | 6/2005 | Coyle et al. .......... 600/538 |
| 2005/0125970 A1 | 6/2005 | Nolan |
| 2005/0211247 A1 | 9/2005 | Noda et al. |
| 2005/0228234 A1 | 10/2005 | Yang ..................... 600/300 |
| 2005/0240087 A1 | 10/2005 | Keenan et al. ........ 600/301 |
| 2005/0256385 A1 | 11/2005 | Diab et al. |
| 2006/0000420 A1 | 1/2006 | Davies et al. |
| 2006/0036183 A1 | 2/2006 | Sackner et al. ........ 600/481 |
| 2006/0074334 A1 | 4/2006 | Coyle |
| 2006/0122528 A1 | 6/2006 | Gal |
| 2006/0178591 A1 | 8/2006 | Hempfling ............ 600/529 |
| 2006/0258914 A1 | 11/2006 | Derchak et al. |
| 2006/0293609 A1 | 12/2006 | Stahmann et al. |
| 2007/0027368 A1 | 2/2007 | Collins et al. |
| 2007/0050715 A1 | 3/2007 | Behar |
| 2007/0100622 A1 | 5/2007 | Tavares |
| 2007/0150006 A1 | 6/2007 | Libbus et al. |
| 2007/0177770 A1 | 8/2007 | Derchak et al. |
| 2007/0208262 A1 | 9/2007 | Kovacs |
| 2007/0209669 A1 | 9/2007 | Derchak |
| 2007/0270671 A1 | 11/2007 | Gal |
| 2008/0015454 A1 | 1/2008 | Gal |
| 2008/0027341 A1 | 1/2008 | Sackner et al. |
| 2008/0045815 A1 | 2/2008 | Derchak et al. |
| 2008/0051839 A1 | 2/2008 | Libbus et al. |
| 2008/0082018 A1 | 4/2008 | Sackner et al. |
| 2008/0221401 A1 | 9/2008 | Derchak et al. |
| 2008/0269644 A1 | 10/2008 | Ray |
| 2009/0131759 A1 | 5/2009 | Sims et al. |
| 2010/0274100 A1 | 10/2010 | Behar et al. |
| 2011/0009766 A1 | 1/2011 | McCool |

FOREIGN PATENT DOCUMENTS

| | | |
|---|---|---|
| EP | 0875199 A | 11/1998 |
| GB | 1596298 A | 8/1981 |
| GB | 2116725 | 9/1983 |
| JP | 53126786 A | 6/1978 |
| JP | 58109031 A | 6/1983 |
| JP | 6337933 A | 2/1988 |
| JP | 1091834 A | 4/1989 |
| JP | 5168602 A | 7/1993 |
| JP | 5298589 A | 11/1993 |
| JP | 7227383 A | 8/1995 |
| JP | 2001516253 A | 9/1998 |
| JP | 2001104259 A | 4/2001 |
| WO | WO9810699 | 3/1998 |
| WO | WO0128420 | 4/2001 |
| WO | WO0176467 | 10/2001 |
| WO | WO02060370 | 8/2002 |
| WO | WO02069878 | 12/2002 |
| WO | WO03022149 | 3/2003 |
| WO | WO2004/019503 | 3/2004 |
| WO | WO 2005/053532 | 6/2005 |
| WO | WO2005/115242 | 12/2005 |
| WO | WO2006002338 | 1/2006 |
| WO | WO2006009830 | 1/2006 |
| WO | WO2007021645 | 2/2007 |
| WO | Wo2007069111 | 6/2007 |
| WO | WO2007089751 | 8/2007 |
| WO | WO2009074973 | 6/2009 |
| WO | WO2010027515 | 3/2010 |

OTHER PUBLICATIONS

Fahrenberg et al., "Origins and Developments of Ambulatory Monitoring and Assessment", Progress in Ambulatory Assessment. Seattle, WA: Hogrefe and Huber (2001).

Brack, "Cheyne-Stokes respiration in patients with congestive heart failure," Swiss Med Wkly, 133: 605-610 (2003).

Costa et al., "Multiscale Entropy Analysis of Complex Physiologic Time Series," Physical Review Letters, 89(6): 068102-1-068102-4 (2002).

Grossman et al., "Reliability of respiratory tidal volume estimation by means of ambulatory inductive plethysmography," Biomed Sci Instrum., 42: 193-198 (2006).

Myers et al., "Rectification and non-linear pre-processing of EMG signals for cortico-muscular analysis," Journal of Neuroscience Methods, 124: 157-165 (2003).

Richman et al., "Physiological time-series analysis using approximate entropy and sample entropy," Am J Physiol Heart Circ Physiol, 278: H2039-H2049 (2000).

Szabó et al., "Prognostic Value of Heart Rate Variability in Chronic Congestive Heart Failure Secondary to Idiopathic or Ischemic Dilated Cardiomyopathy," The American Journal of Cardiology, 79(7): 978-980 (1997).

Eric M. Snyder et al., Ventilatory Responses to Hypoxia and High Altitude During Sleep in Aconcagua Climbers:, Wilderness and Environmental Medicine, vol. 18, pp. 138-145 (2007).

International Search Report PCT/US07/71562 dated Jul. 25, 2008.

6th Portuguese Conference on Biomedical Engineering, "BioEng' 2001 Conference Papers", (Jun. 2001) 6 pages.

Aliverti. et al., "Chronic Obstructive Pulmonary Disease: Regional Chest Wall Volumes During Exercise in Chronic Obstructive Pulmonary Disease." *Thorax*, 59:210-216, 7 pages, 2004.

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al., "Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

National Biometric Test Center, "The Functions of Biometric Identification Devices", *San Jose State University Biometrics Publications*, www.engr.sjsu.edu/biometrics/publications_tech.html (printed Jul. 28, 2005), 25 pages.

National Biometric Test Center, "Biometric Technology—Testing, Evaluation, Results", *San Jose State University Biometrics Publications*, www.engr.sjsu.edu/biometrics/publications_tech.html (printed Jul. 28, 2005), 13 pages.

Blechert et al., "Identifying Anxiety States Using Broad Sampling and Advance Processing of Peripheral Physiological Information," *Psychosom Med* Dec. 2007; 69(9):935-43 EPUB Nov. 8, 2007, 6 pages.

Bloch et al., "Specific respiratory patterns distinguish among human basic emotions," *International Journal of Psychophysiology*, 11:141-154 (1991), 14 pages.

Bonnet et al., "EEG Arousals: Scoring Rules and Examples, A Preliminary Report from the Sleep Disorders Atlas Task Force of the American Sleep Disorders Association," *Sleep*, 152(2): 173-184 (1992), 12 pages.

Brack, "Cheyne-Stokes respiration in patients with congestive heart failure," Swiss Med Weekly 133:605-610 (2003), 7 pages.

Costa et al., "Multiscale Entropy Analysis of Complex Physiologic Time Series," Physical Review Letters 89(6):068102-1-4 Aug. 5, 2002, 4 pages.

Coyle et al., "Home Measurement of Cough Indicates Circadian Frequency Pattern and Abnormal Distribution During Sleep," LifeShirt System, study sponsored by Pfizer, Inc., Jun. 2004, 1 page.

Fahrenberg, "Origins and Developments of Ambulatory Monitoring and Assessment," (2001), 30 pages.

Gore Electronic Products, "Expanded PTFE Insulation Material", www.goreelectronics.com (visited Aug. 2005), 4 pages.

Grossman et al., "Reliability of Respiratory Tidal Volume Estimation by Means of Ambulatory Inductive Plethysmography," Biomed Sci Instrum 42:193-8 (2006), 6 pages.

Grossman et al., "A Comparison of three Quantification Methods for Estimation of Respiratory Sinus Arrhythmia", Psychophycology, 27(6):702-714 (1990), 17 pages.

Istepanian et al., "Microcontroller-Based Underwater Acoustic ECG Telemetry System", IEEE Transactions on Information Technology in Biomedicine, 1(2):150-154 (Jun. 1997), 5 pages.

Keennan et al., "Adaptive Filtering of Heart Rate Signals for an Improved Measure of Sympathovagal Balance," Jan. 1, 2005, 8 pages.

Klabunde, "Electrocardiogram (EKG, ECG)", Cardiovascular Physiology Concepts, www.cvphysiology.com (visted Mar. 2005), 3 pages.

Lake et al., "Sample entropy analysis of neonatal heart rate variability," Am J Physiol Regul Integr Comp 283:R789-97 (2002), 10 pages.

Marin et al., "Inspiratory Capacity, Dynamic Hyperinflation, Breathlessness, and Exercise Performance During The 6-Minute-Walk Test in Chronic Obstructive Pulmonary Disease", Am. J. Respir. Crit. Care Med., vol. 163., pp. 1395-1399, (2001), 5 pages.

McCool et al., "Estimates of ventilation from body surface measurements in unstricted subjects," J. Appl. Physiol. 61(3):1114-9 (1986), 6 pages.

McCool et al., "Tidal Volume and Respiratory Timing Derived from a Portable Ventilation Monitor," Chest 122:684-91 (2002), 10 pages.

McNaughton et al., "Metallized Polymer Fibers as Leadwires and Intrafascicular Microelectrodes", J. Neurosci. Methods, 70(1):103-10 (1996), 2 pages.

Micro-Coax, "About Micro-Coax", www.micro-coax.com (visited Aug. 2004), 9 pages.

Niskanen et al., "Software for Advanced HRV Analysis", University of Kuopio Department of Applied Physics Report Series, pp. 1-11 (Feb. 2002), 12 pages.

O'Donnell, "Ventilatory Limitations in Chronic Obstructive Pulmonary Disease", Medicine & Science in Sports & Exercise, pp. S647-S655, (2001), 9 pages.

O'Donnell et al., "Dynamic Hyperinflation and Exercise Intolerance in Chronic Obstructive Pulmonary Disease", Am. J. Respir. Crit. Care Med., 164:770-777 (2001), 8 pages.

Park et al., "Automated Detection and Elimination of Periodic ECG Artifacts in EEG Using the Energy Interval Histogram Method", IEEE Transactions on Biomedical Engineering 49(12):1526-1533 (2002), 8 pages.

Pietraszek et al., "Simple Telemetry System for ECG Recording", Polish J. Med. Phys. & Eng. 2002; 8(3): 193-198, 4 pages.

Rampil, "A Primer for EEG Signal Processing in Anesthesia," Anesthesiology 89(4):980-1002 Oct. 1998, 15 pages.

Richman et al., "Physiological time-series analysis using approximate entropy and sample entropy," Am J. Physiol Circ Physiol 278:H2039-49 (2000), 11 pages.

Signal Consulting Inc., "Inductance of Circular Loop", www.sigcon.com (visited Aug. 2005), 2 pages.

Sijbers et al., "Reduction of ECG and gradient related arifacts in simultaneously recorded human EEG/MRI data," Magnetic Resonance Imaging 18:881-6 (2000), 6 pages.

Snyder et al., "Ventilatory Responses to Hypoxia and High Altitude During Sleep in Aconcagua Climbers," Wilderness and Environmental Medicine 18:138-145 (2007), 8 pages.

Szabo et al., "Prognostic Value of Heart Rate Variability in Chronic Congestive Heart Failure Secondary to Idiopathic or Ischemic Dilated Cardiomyopathy," Am J Cardiol. 79:978-980 (1997), 3 pages.

Taylor, et al., "Cigarette smoke inhalation patterns and bronchial reactivity", 1988, Thorax, 43, 65-70.

van Dijk et al., "Determinants of Brachial Artery mean 24 h PulsePressure in Individuals with Type II diabetes mellitus and untreated mild hypertension", Clinical Science (2002), 102, pp. 177-186, 10 pages.

Vogiatzis, et al., "Respiratory Kinematics by Optoelectronic Plethysmography During Exercise in Men and Women.", Eur J of App Physiol, 581-587, 7 pages, 2004, 7 pages.

Wachowski, Andy and Larry, The Matrix, released Mar. 31, 1999 by Warner Bros. Pictures, see 1:26:29, 2:03:10, and 2:04:41, 13 pages.

Wilhelm et al., "Distinguishing Emotional from Physical Activation in Ambulatory Psychophysiological Monitoring," Biomed Sci Instrum 42:458-63 (2006), 6 pages.

Wilhelm et al., "Taking the laboratory to the skies: Ambulatory assessment of self-report, autonomic, and respiratory responses in flying phobia," Psychophysiology 35:596-606 (1998), 11 pages.

Supplementary Partial European Search Report of the European Patent Office, Application No. EP 06784447.2, dated Jan. 20, 2010, 9 pages.

Supplementary Partial European Search Report of the European Patent Office, Application No. EP 04759405.6, dated Jan. 25, 2011, 4 pages.

International Search Report and the Written Opinion of the International Searching Authority, application No. PCT/US2008/061171, dated Nov. 14, 2008, 10 pages.

International Search Report and the Written Opinion of the International Searching Authority, application No. PCT/US06/60264, dated Jan. 15, 2008, 8 pages.

International Search Report and the Written Opinion of the International Searching Authority, application No. PCT/US2007/82688, dated May 8, 2008, 7 pages.

International Search Report and the Written Opinion of the International Searching Authority, application No. PCT/US2008/072414, dated Nov. 12, 2008, 7 pages.

Extended European Search Report for Application No. EP 07798146.2, Applicant: adidas AG, mailed Oct. 19, 2010.

Extended European Search Report for Application No. EP 10174873.9, Applicant: adidas AG, mailed Dec. 8, 2010.

Extended European Search Report for Application No. EP 10174680.8, Applicant: adidas AG, mailed Dec. 9, 2010.

Extended European Search Report for Application No. EP 10174876.2, Applicant: adidas AG, mailed Dec. 9, 2010.

Extended European Search Report for Application No. EP 10174881.2, Applicant: adidas AG, mailed Dec. 9, 2010.

Extended European Search Report for Application No. EP 10174683.2, Applicant: adidas AG, mailed Dec. 27, 2010.

Partial European Search Report for Application No. EP 10174885.3, Applicant: adidas AG, mailed Jan. 4, 2011.

Office Action dated Nov. 30, 2010 from Japanese Appl. No. 2006-509897, Adidas AG, Systems and Methods for Respiratory Event Detection, with translation.

Office Action dated Aug. 2, 2010 from U.S. Appl. No. 11/373,822, Sackner, System and Methods for Ambulatory Monitoring of Physiological Signs, filed Mar. 9, 2006.

Office Action dated Sep. 28, 2010 from U.S. Appl. No. 11/503,350, Behar, Systems and Methods for Monitoring Subjects in Potential Physiological Distress, Aug. 10, 2006.

Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.

Office Action dated Nov. 18, 2010 from U.S. Appl. No. 11/492,484, Behar, Computer Interfaces Including Physiologically Guided Avatarss, filed Jul. 24, 2006.

Office Action dated Jan. 4, 2011 from U.S. Appl. No. 11/233,317, Gal, Improved Sensors for Inductive Plethysmographic Monitoring Applications and Apparel Using Same, Sep. 21, 2005.

Office Action dated Jan. 27, 2011 from U.S. Appl. No. 10/991,877, Keenan, Method and system for processing data from ambulatory physiological monitoring, Nov. 18, 2004.

Office Action dated Feb. 2, 2011 from U.S. Appl. No. 11/373,822, Sackner, Systems and methods for ambulatory monitoring of physiological signs, Mar. 9, 2006.

Office Action dated Feb. 17, 2011 from U.S. Appl. No. 11/682,601, Derchak, Monitoring and quantification of smoking behaviors, Mar. 6, 2007.

U.S. Appl. No. 11/357,772, Sackner, System and Methods for Ambulatory Monitoring of Physiological Signs, filed Feb. 17, 2006.

U.S. Appl. No. 11/373,822, Sackner, System and Methods for Ambulatory Monitoring of Physiological Signs, filed Mar. 9, 2006.

U.S. Appl. No. 12/869,576, Stone, Method and System for Limiting Interference in Magnetometer Fields, filed Aug. 26, 2010.

U.S. Appl. No. 12/869,578, Derchak, Noninvasive Method and System for Monitoring Physiological Characteristics, filed Aug. 26, 2010.

U.S. Appl. No. 12/869,582, Derchak, Noninvasive Method and System for Monitoring Physiological Characteristics and Athletic Performance, filed Aug. 26, 2010.

Lippman, N., et al., "*Comparison of methods for removal of ectopy in measurement of heart rate variability,*" Am. J, Physiol. 267 (1 Pt.2): H411-18, The American Physiological Society (1994).

Malik, M., "*Heart rate variability standards of measurement, physiological interpretation, and clinical use,*" Eur. Heart J. 17: 354-381, American Heart Association Inc.; European Society of Cardiology (1996).

Paradiso, R., et al., "*Knitted Bioclothes for Cardiopulmonary Monitoring,*" Conf. Proc. IEEE ENG. Med. Biol. Soc. 4: 3720-23, European Commission (2003).

Pincus, S. M., "*Approximate entropy as a measure of system complexity,*" Proc. Natl. Acad. Sci. USA 88: 2297-2301, The Proceedings of the National Academy of Sciences USA (1991).

Richman, J. S., et al., "*Physiological time-series analysis using approximate entropy and sample entropy,*" Am. J. Physiol. Heart Circ., Physiol. 278: H2039-49, The Amercian Physiological Society (2000).

Sackner M.A., "*A simple and reliable method to calibrate respiratory magnetometers and repitrace,*" J. Appl. Physiol. 81: 516-17, The American Physiological Society (1996).

Spencer, K. T., MD, et al., "*Diastolic heart failure what primary care physicians need to know,*" Postgrad. Med. 101: 63-65, University of Chicago (1997).

Tabachnik, E., M.B., Ch.B, et al., "*Measurement of ventilation in children using the respiratory inductive plethysmograph,*" J Ped. 99: 895-99, The C.V. Mosby Co (1981).

\* cited by examiner

AUTOMATIC AND AMBULATORY MONITORING OF CONGESTIVE HEART FAILURE PATIENTS

CROSS REFERENCE TO RELATED APPLICATIONS

This application claims the benefit of U.S. provisional application No. 60/815,367 filed Jun. 20, 2006, which is included herein by reference in its entirety for all purposes.

FIELD OF THE INVENTION

The present invention is related to the field of physiological monitoring, and in particular to methods and systems sensitive to the cardiac status of a patient with congestive heart failure (CHF). In preferred embodiments, the physiological monitoring system is non-invasive and is sufficiently lightweight and unobtrusive so that it can be carried by a patient without preventing normal daily activities.

BACKGROUND OF THE INVENTION

Congestive heart failure (CHF), or simply heart failure, is a condition in which a damaged heart muscle is unable to pump sufficient blood to meet the body's demands, first in the early stages, only during exercise, but later in advanced stages, even during rest. It is an important and common disease having numerous etiologies and afflicting millions of Americans with up to 400,000 new cases yearly. It is the most common diagnosis in hospital patients over 65.

It is well known that CHF patients, although usually stable, can nevertheless decompensate from time-to-time, even to the extent that their life may be threatened by, e.g., hypotension or pulmonary edema. Decompensation typically occurs because proper functioning of the cardiovascular system requires that cardiovascular parameters be in balance, and although this balance is routinely maintained in health by normal physiological controls, the normal controls can become inadequate in CHF. Medical treatment is then necessary to restore the cardiovascular system to balance and to maintain it in balance. But balance achieved by medical treatment is often not robust and can be easily disturbed. CHF patients have insufficient cardiovascular reserve with which to compensate for unexpected or unpredicted variation in their medical treatments. A CHF patient who is controlled one week, may decompensate the following week.

Such variations in medical treatment can be all too common events. According to current practice, CHF treatment generally includes encouraging advantageous nutritional and lifestyle habits along with prescribing cardiovascular active drugs when necessary. It is well known that patient behavior, such as nutrition and lifestyle, is notoriously unpredictable and resistant to change. For example, although a patient may be well aware that, because fluid overload readily occurs in CHF, it is advisable to limit salt and water intake, that patient may from time to time ingest excessive salt and decompensate. Also, although the patient is aware that lower body weight and cessation of smoking are highly desirable, the patient may nevertheless from time-to-time overeat and smoke. Both these behaviors, if continued over time, can lead to decompensation.

Less well known, perhaps, is that maintaining a proper dose of cardiovascular active drugs can be equally difficult. Drugs, which at one dose usefully treat CHF, can, at another dose, exacerbate CHF. For example, diuretics can cause potassium deficiency which leads to abnormal cardiac rhythms and decreased cardiac output. Digitalis, an important drug in CHF, has a narrow therapeutic range. If too much digitalis accumulates in the blood, it can become toxic instead of therapeutic. A forgetful patient skipping a dose, doubling a dose, or otherwise taking improper doses can decompensate.

It is apparent, therefore, that automatic methods and systems that can monitor CHF patients for signs of decompensation can be useful for managing their treatments and maintaining their health. It is further apparent that such monitoring methods and systems can be even more useful if patient monitoring is possible without expert assistance and while patients perform their normal daily activities. Such cardiovascular monitoring systems capable of useful monitoring of CHF patient during their normal daily activities are not believed to be known in the prior art.

Citation or identification of any reference in this section or in any section of this application shall not be construed as an admission that such reference is available as prior art to the present invention.

SUMMARY OF THE INVENTION

Accordingly, objects of the present invention include methods and systems for cardio-respiratory monitoring of patients with congestive heart failure (CHF) and for processing cardio-respiratory monitoring data for signs indicating likely decompensation of a patient. Further objects include such methods and systems that can be used by patients without expert assistance and during their normal daily activities. The present invention provides such methods and systems, and accordingly, has considerable use in the care of CHF patients.

This invention is based in part on the inventor's understanding that CHF effects a number of parameters of a patient's cardiac and respiratory functioning that can be non-invasively measured, and further that measurements of these parameters can be interpreted to provide useful information concerning the patient's CHF, e.g., concerning its severity and/or stability. Accordingly, this invention provides methods that determine one or more of these parameters from physiological monitoring data, and methods that produce information concerning that patient's CHF by comparing and correlating determined parameters. This invention also preferably includes ambulatory systems for gathering physiological monitoring data that permit a monitored patient to engage in substantially all their normal daily activities, whatever these activities might be. These systems preferably include one or more computing devices that perform this invention's methods and make results available locally to the patient and remotely to the patient's caregiver.

Several such non-invasively measurable CHF parameters are known, including periodic breathing (PB); heart rate variability (HRV). Preferred embodiments determine at least one of these parameters, preferably both. Other preferred parameters are indices of cardiac output (CO), activity and posture, blood oxygen saturation or partial pressure, and spO2. This list is not limiting and additional parameters can be determined in further embodiments. These preferred parameters are now summarized.

PB, also known as Cheyne-Stokes respiration (CSR), refers to a breathing pattern characterized by periodically-occurring cycles during which a period of normal breathing or possible increased breathing (hyperpnea) is followed by a period of decreased breathing (hypopnea: a tidal volume (Vt) of 10-30% of a patient's recent average Vt). Breathing may even periodically cease (apnea: a Vt of 0-10% of a patient's recent average Vt). PB is known to be associated with CHF and also known to be a risk factor for worsening CHF and reduced survival. See, e.g., Brack, 2003, Cheyne-Stokes respiration in patients with congestive heart failure, *Swiss Med. Wkly.* 133:605-610. PB is particularly significant if it occurs when a patient's spO2 is substantially within normal limits (normoxia).

Periodic breathing is preferably detected and measured by analyzing the temporal sequence of a patient's lung volumes, minute ventilation, or in particular, their tidal volumes. An episode of PB can be characterized by its duration and by the amplitude and length of the cycles of the patient's Vt (or other respiratory measure). A patient can be characterized by the amount of time during a day during which PB (of a selected degree of severity) is detected.

Heart rate variability (HRV) refers to the beat-to-beat alterations in heart rate. At rest, the ECG of healthy individuals generally exhibits periodic variation in R-R intervals in association with respiration, an effect known as respiratory sinus arrhythmia (RSA). RSA reflects a balance of the autonomic nervous system with parasymphathetic activity (carried via the vagal nerve) predominates in comparison to sympathetic activity. During periods when the heart is subject to stress or greater load, RSA decreases as sympathetic activity comes to predominate in comparison to parasymphathetic activity.

During CHF, the heart is chronically stressed to maintain needed levels of output; sympathetic activity increases, and HRV (and RSA) typically decreases. See, e.g., Camm et al., 1996, Heart rate variability—standards of measurement, physiological interpretation, and clinical use, *Eur. Heart J.* 17:354-381. Further, the degree of HRV reduction in CHF has been found to correlate with the severity of the CHF and to an increased risk of cardiac death. See, e.g., Szabo et al., 1997, Prognostic value of heart rate variability in chronic congestive heart failure secondary to idiopathic or ischemic cardiomyopathy, *Am J. Cardiol.* 79:978-80.

HRV can be detected and measured by analyzing the temporal sequence of RR intervals observed in the electrocardiogram (ECG). Known analysis methods include time-domain methods, which use directly the distribution of measured RR intervals. Also known are spectral methods, which transform the sequence of measured RR intervals into a frequency spectrum of the interval distribution. It is important that cardiac rate data input to an HRV determination be free of irregularities. This invention provides methods that detect irregularities in breathing and therefore induced cardiac irregularities. The provided methods examine raw or filtered sensor signals and not derived respiratory parameters, such as tidal volumes.

Turning to the other preferred parameters, cardiac output (CO), that is the volume of blood pumped by the heart in a unit of time normalized by body size, is particularly advantageous. For example, a typical CO for a healthy adult is approximately 5-6 liters per minute per square meter of body surface and during vigorous exercise can increase by perhaps five-fold. It is well known that chronically reduced cardiac output (CO) is a hallmark of CHF. Its value reflects the severity of the disease, and decreases further as the disease progresses. For example, in severe disease, CO may be only 2.5 liters/min/m2 without any exercise reserve. Further, acute reductions of CO are known to often precipitate or occur with acute decompensation of a patient's CHF. See, e.g., Kirk et al., 1997, Diastolic heart failure, *Postgraduate Medicine* 101 (1).

Although CO cannot be directly measured by non-invasive means, it can be determined as the product of stroke volume (SV) and heart rate (HR), or from indicia of SV and HR. A suitable SV indicia should be non-invasively measurable and also should be related with statistical significance to actual SV as determined by standard invasive clinical methods. Such an indicia can be extracted from the amplitudes of the cardiac-related pulsations of the anterior chest, e.g., chest pulsation at the level of the xiphoid process, and these pulsations can be determined from the non-invasively measured sizes of the anterior chest. The amplitude of these pulsations can then be calibrated to provide an indicia of CO and/or ejection fraction. This process of providing an indicia of SV from chest-size changes is referred to herein as thoraco-cardiography (TCG).

Activity and posture and spO2 can be readily measured by non-invasive means: activity and posture and be extracted from accelerometer data; and spO2 data is output by a pulse oximeter at a selected location, e.g., the thumb, the earlobe, and so forth. These preferred parameters provide useful patient baseline information against which changes in the other parameters can be assessed. For example, it is more ominous, e.g., for PB to be present even when the spO2 is normal, or for spO2 to be decreased even when resting in a chair.

Next, preferred monitoring systems for use in this invention can be used by monitored patients without expert assistance and further permit monitored patient to engage in substantially normal daily activities with few or no restrictions (referred to herein as "ambulatory monitoring"). However, it should be noted that although primarily directed to ambulatory monitoring of CHF patients, the methods of this invention are also useful for processing physiological activity data from other types of monitoring systems, e.g., hospital systems that are not portable. It should also be noted that the functional significance of the term "ambulatory monitoring", that is monitoring during normal daily activities, varies widely from patient to patient. Some CHF patients with early or mild disease may be able to perform most activities other than moderate exercise, while other CHF patients with late or severe disease may require extensive bed rest. The term "ambulatory monitoring" during normal daily activities is to be understood as applying to both classes of CHF patients. In the following, for compactness only and without restriction or limitation, this invention will be described in its preferred embodiments for ambulatory monitoring.

Suitable ambulatory monitoring systems can be based on monitoring garments (generally, items of clothing) which directly incorporate physiological sensors into their construction or which carry, support, or have attached physiological sensors. Suitable garments are preferably similar to everyday clothing items, are normally fitting, and are readily put-on or donned by patients. For example, garments can be configured as vests, shirts, pants, shorts, head bands, chest bands, straps, and the like (and including shoes, watches, bracelets, and so forth). The sensors incorporated or carried by a garment are preferably ready for operation after the garment is donned and with little or no attention or adjustment by the monitored patient. Preferred sensors are responsive to changes in chest volumes that are primarily respiratory and/or cardiac in origin and to ECG signals. Optional but preferred sensors are responsive to spO2 and to patient posture and activity (e.g., an accelerometer).

Preferred monitoring system also include a lightweight, unobtrusive and autonomously operating electronic module or processing device that can be carried by a monitored patient, e.g., in a pocket or attached to a belt, and is capable of processing sensor data and wirelessly communicating this data for real-time use of storing data for offline analysis. Preferred devices are capable of performing some or all the methods of this invention. Such a device will generally includes circuitry to operate sensors, retrieve sensor data, and transmit and/or retrieved data. Processing circuitry can include microprocessors with storage for program code or configurable circuits such as FPGAs loaded with configuration firmware. Such a device is preferably battery powered.

A preferred ambulatory monitoring system is capable of monitoring tidal volume, the relative contributions of rib cage and abdominal expansion to tidal volume, heart rate, ECG, motion, blood oxygen saturation, posture, and activity. Such systems, for example the LifeShirt® system, are available from VivoMetrics, Inc., Ventura, Calif.

Finally, in an exemplary patient monitoring scenario, the duration of ambulatory monitoring will normally vary depending of the severity and stability of the patient's CHF. If the patient has stable and mild CHF, it may be sufficient to monitor two or three days per week. If the patient has unstable or severe disease, ambulatory monitoring may be nearly continuous monitoring, even during sleep. The monitoring system gathers respiratory and ECG and preferably also thoraco-cardiogram, SpO2, and patient activity data. An accompanying autonomous electronic module then processes the retrieved respiratory and spO2 data to identify PB, the number of PB episodes, the total duration of PB during, e.g., a day, and characteristics of the PB pattern. The retrieved ECG data (aided by the respiratory data) is then processed to identify HRV, the degree of HRV, and how HRV varies during, e.g., a day. The retrieved thoraco-cardiogram data is also processed to identify indicia of CO and any chronic or acute changes in CO. The retrieved activity data is processed to obtain indicia of the patient's activity levels and optionally postures. Some of all of the processed data is preferably made available online to the patient's physician/caregivers by, e.g., wireless transmission. Raw data can also be wirelessly transmitted or, alternatively, stored on removable memory (optionally along with processed data).

Therefore, it can be appreciated that ambulatory monitoring systems, such as the LifeShirt system, can be used to monitor and identify changes in congestive heart failure. Raw and analyzed monitoring data can be provided to physicians and other caregivers on a regular basis and enable more rapid and targeted interventions with patients. Rapid and appropriate intervention, especially in emergency situations, will generally improve the quality of life for CHF patients and reduce costs of their treatments.

BRIEF DESCRIPTION OF THE DRAWINGS

The present invention may be understood more fully by reference to the following detailed description of the preferred embodiment of the present invention, illustrative examples of specific embodiments of the invention and the appended figures in which.

DETAIL DESCRIPTION OF THE PREFERRED EMBODIMENTS

Preferred embodiments of the invention are now described in more detail. This section describes first methods for the analysis of periodic breathing (PB), then methods of analysis of heart rate variability (HRV), and finally system implementations of the methods of this invention. Alternative embodiments also include data from thoraco-cardiogram signals (TCG). In the following (and in the application as a whole), headings and legends are used for clarity and convenience only.

Analysis of Periodic Breathing (PB)

Figure 1A:
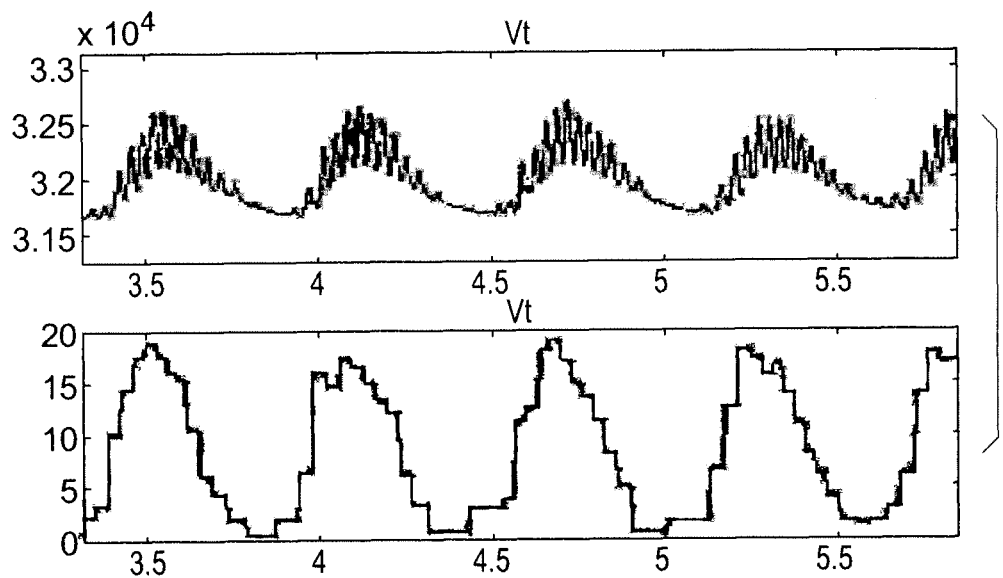
FIGS. 1A-B illustrate examples of periodic breathing.
Figure 1B:
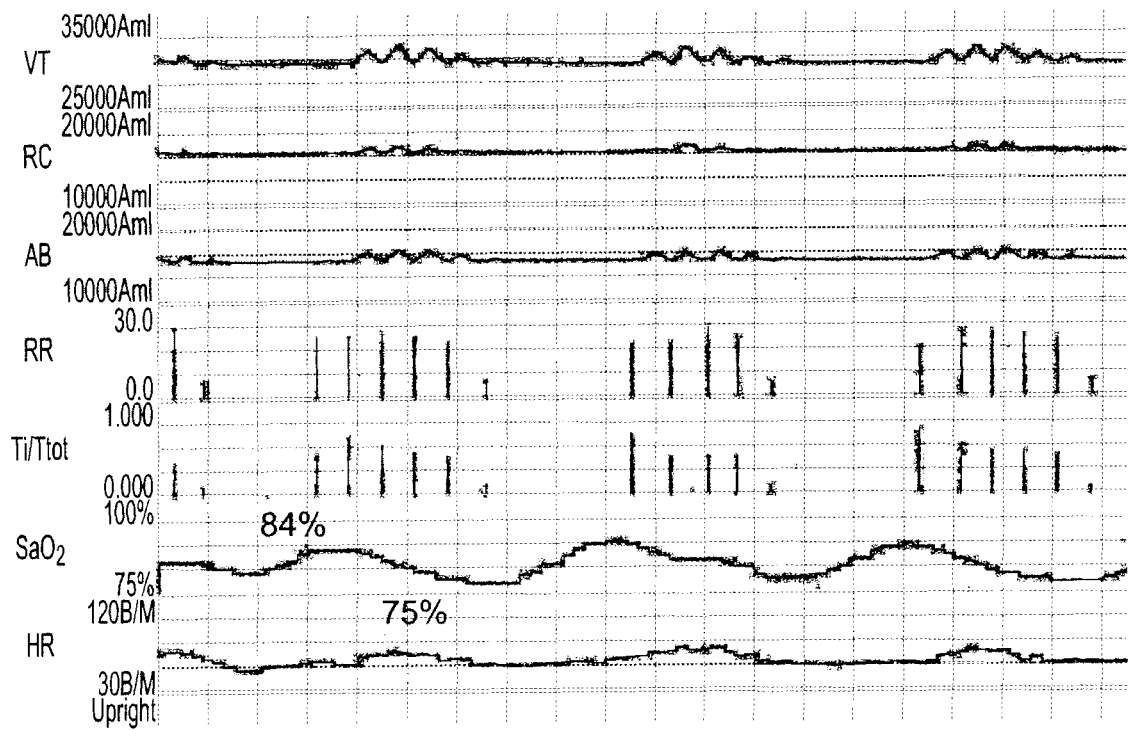

FIGS. 1A-B illustrate two examples of PB measured in monitored subjects. The horizontal scale in FIGS. 1A-B is time. FIG. 1A illustrates significant periodic breathing in a CHF patient over a 2 minute period. Here, the upper trace represents moment-by-moment lung volumes (Vt), and the lower trace represents minute ventilation (VE). From the upper trace, it is apparent that volumes of individual breaths waxes and wanes in a manner characteristic for PB. Also, this subject's residual lung volumes increase during periods of increased breathing and decrease during periods of decreased breathing. From the lower trace, it is apparent that VE also varies regularly between an upper value and a lower value that is approximately zero. FIG. 1B illustrates pronounced PB in a healthy patient at high altitude and acutely hypoxic (reduced SaO2). The upper trace, representing Vt, reveals that this subject actually ceases breathing (apnea) between periods of reduced breathing. The other traces in this figure represent the parameters: RC and AB represent rib case size and abdominal size; VT (Vt) is the lung volume which here is a combination of the RC and AB traces; RR represents respiration rate; Ti/Tot represents the inspiratory time (Ti) divided by the total breath time (Tot); SaO2 represent blood oxygen saturation; and HR represents heart rate. Vt can be closely estimated as a linear combination of RC and AB, and VE is then Vt times respiration rate.

This invention provides multiple PB analysis methods. All embodiments implement at least one PB method, while preferred embodiments implement two or more methods and compare their output for increased accuracy. Output can be combined by a voting scheme, by finding a median or average, and the like. Input respiratory signals can represent moment-by-moment lung volumes known (referred to as tidal volume (Vt) signals). Other respiratory input can be derived from Vt signals on a breath-by-breath basis. For example, the volumes of an individual breath (also referred to as a "tidal volume" and abbreviated "Vt") can be derived by subtracting the end-inspiratory lung volume from the following end-expiratory lung volume as observed in moment-by-moment Vt signals. Then, a sequence of VE values can be derived from the sequence of Vt values by multiplying by the breath rate. Input signals to most analysis methods are preferably resampled to a fixed, common rate. Also, signals are divided into successive overlapping windows, and the presence or absence of PB is determined window-by-window. For example, windows can include tens to hundreds to thousands of individual breaths and can be periodically placed at intervals of 10% to 90% of the window width.

Provided PB analysis methods process can be categorized as time-domain methods, frequency-domain methods, or non-linear methods. Time domain methods generally process derived respiratory data such as tidal volumes or minute ventilation (VE), which is a product of tidal volume of individual breaths and the rate of individual breaths (e.g., the inverse of the time interval between adjacent breaths), and the durations of individual breaths (Tot). Minute ventilation is an advantageous input since it depends on both breath volumes and breath durations. Frequency-domain methods generally process primary respiration signals, i.e., RC and AB signals.

Simple time domain methods use statistical techniques to represent the variability of tidal volumes of individual breaths. For example, values of coefficients of variation, or standard deviations, or root mean squares, or the like can be determined for each window of data. It is then expected that PB can be distinguished from regular respiration by larger values of such variability measures.

Preferred time domain methods include methods based on autocorrelation. Autocorrelation methods correlate the data in each window with the same data that is shifted by multiples of a selected time interval (e.g., 5, 15, 30, 60, and more seconds). The breath data can be used as measured, or can be resampled to an even rate. Correlation involves computing the sum of the products of each data value in a window with the data value occurring at the selected time interval (shift) earlier or later, and then normalizing by the unshifted correlation, i.e., the data in the window is correlated (multiplied) with itself. The resulting normalized correlations are bounded between −1 and +1. The significance of a particular correlation value can be estimated with reference to the probability distribution (e.g., a normalized histogram) of the computed correlation values. For example, the significance of a computed correlation is determined by how many standard deviations it differs from the average correlation value. The probability distribution can represent correlation data from many or all windows, or can be limited to data from a single window. A 95% significance threshold is used herein; other thresholds can be chosen as necessary.

Figure 2A:
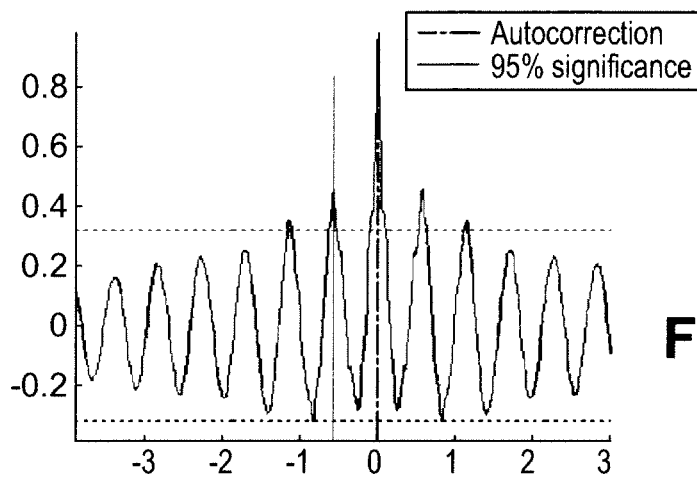
FIGS. 2A-F illustrate results of periodic breathing methods of this invention.

FIG. 2A illustrates the results of an exemplary autocorrelation method applied to a VE signal, where normalized correlation values from multiple data windows are plotted against their corresponding shifts in minutes (a correlogram). Briefly, an individual VE value is determined breath by breath, e.g., as the product of the tidal volume time and the respiratory rate, and then the individual VE values are assembled into a sequence of VE values, each value in the sequence representing VE is determined at the time of successive breaths. This sequence is then resampled at a selected, fixed sampling rate to form a VE signal. The periodic peaks in the correlogram occur at shifts corresponding to the period of the PB pattern, i.e., the interval between two periods of increased (or decreased) breathing. Here three correlation values are significant, the unshifted correlation and the correlations for shifts ±0.9 (arbitrary units). It can be concluded that significant PB is occurring during these data windows, and that the PB has a period of approximately 0.6 sec.

FIGS. 2B-E illustrate examples of processing minute ventilation (VE) signals by preferred frequency domain methods. It should be noted that a VE signal primarily represents changes in overall respiration. Changes accompanying each breath, e.g., inhalation and exhalation, are suppressed because each breath is represented solely by it's tidal volume. Accordingly, spectral analysis of a VE signal should show larger components at frequencies at which overall respiration changes, e.g. PB frequencies, but show smaller components as base respiration frequencies. Further, it should be noted that the horizontal scale of FIG. 2D, 0-0.25 Hz, is expanded in comparison to the scales of FIGS. 2B, 2C, and 2E, which are 0-0.35 Hz, 0-0.45 Hz and 0-0.4 Hz, respectively.

Figure 2B:
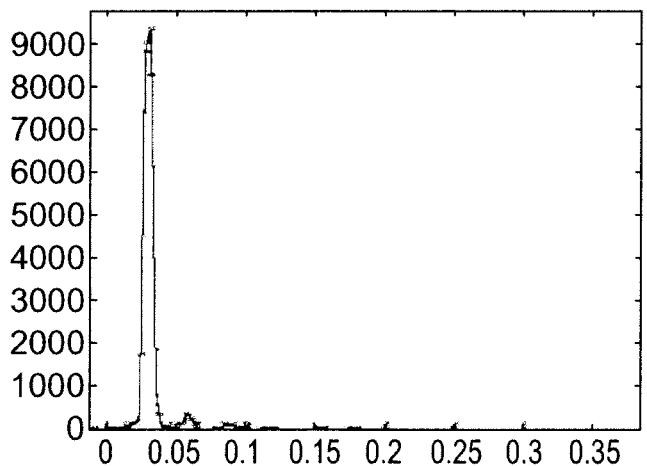

Preferred frequency domain methods also include methods employing spectral transformation methods, such as a fast Fourier transform (FFT), and methods not employing such transforms. A first frequency-domain transform method applies an FFT to windowed data and then forms a periodogram from the transform coefficients by the Welch method. Input data is preferably resampled to a constant, periodic rate chosen to avoid aliasing. Appropriately resampled data is then de-trended and grouped into Hamming windows having 65% overlap (other overlaps and known windowing schemes are also applicable). Preferable window sizes accommodate the chosen transform method, e.g., a power of 2 for the FFT. FIG. 2B illustrates the results of an exemplary FFT-Welch method. In FIGS. 2B-E, the vertical scale is spectral power and the horizontal scale is frequency in Hertz. The high-amplitude transform coefficients at a frequency of approximately 0.03 Hz clearly indicate the presence of significant PB. The much smaller peaks at frequencies of about 0.06 Hz and 0.08-0.09 Hz are thought to represent the frequencies of individual breaths (or harmonics of the fundamental PB period).

Figure 2C:
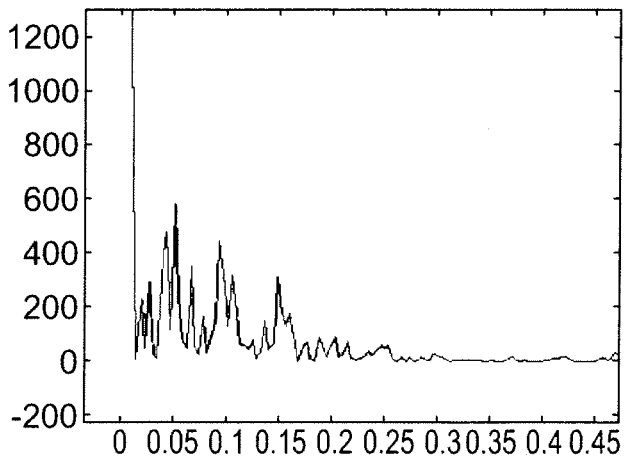

As a control, FIG. 2C illustrates an exemplary FFT-Welch method applied to normal respiratory VE signal without PB. It is seen that the only significant transform coefficient is at approximately zero frequency. The coefficients between 0 and 0.03 Hz have amplitudes less than about 7% of the amplitude of the 0.03-Hz peak in FIG. 2B and do not separate into identifiable discrete frequencies. FIG. 2C readily indicates there is no periodic component to this breathing. Therefore, the presence or absence of PB can be ascertained from the FFT-Welch method applied to VE signals by the presence or absence of a spectral power (proportional to the square of the FFT coefficients) limited to a relatively small frequency band about a principal frequency that is likely to be a PB frequency. If PB is present, the position of the principal (largest amplitude) coefficient indicates the principal PB frequency, and its value indicates the PB amplitude.

It should be noted that the spectral power during PB is limited to a relatively small frequency band, while spectral power during normal breathing decreases across a relatively broad band. These behaviors generally mean that PB is more ordered and more regular while normal breathing is less ordered and less regular.

Figure 2D:
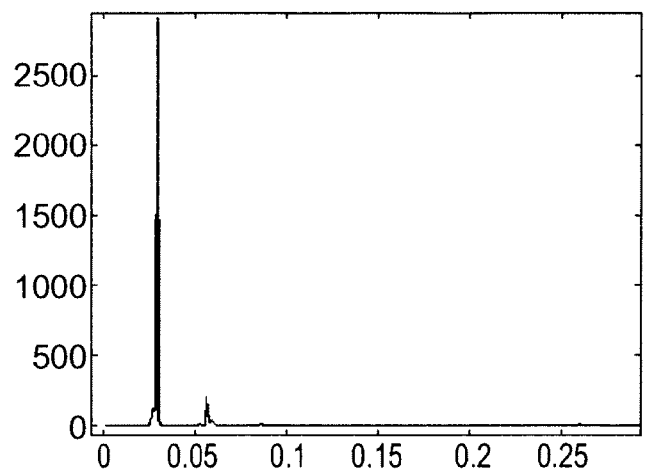

Another frequency-domain transform method, the Lomb-Scargle method (as known in the art), does not require that input data be sampled at a regular, constant rate, and thereby avoids the smoothing and biasing inevitably introduced by resampling. Briefly, the Lomb-Scargle method fits sinusoids to the irregularly sampled input data by the method of least squares. FIG. 2D illustrates the results of an exemplary Lomb-Scargle method applied to a VE signal. Comparing FIG. 2D with 2B, it is apparent that both figures identify the PB frequency, with this frequency being more precisely identified in FIG. 2D as expected in the absence of data resampling. The much smaller peak at about 0.06 Hz (thought to represent the frequencies of individual breaths or harmonics of the fundamental PB period) is also more sharply defied in FIG. 2D that in FIG. 2B. Again, the presence or absence of PB can be ascertained from the Lomb-Scargle method applied to VE signals by the presence or absence of a spectral power limited to a relatively small frequency band about a principal frequency that is likely to be a PB frequency.

Figure 2E:
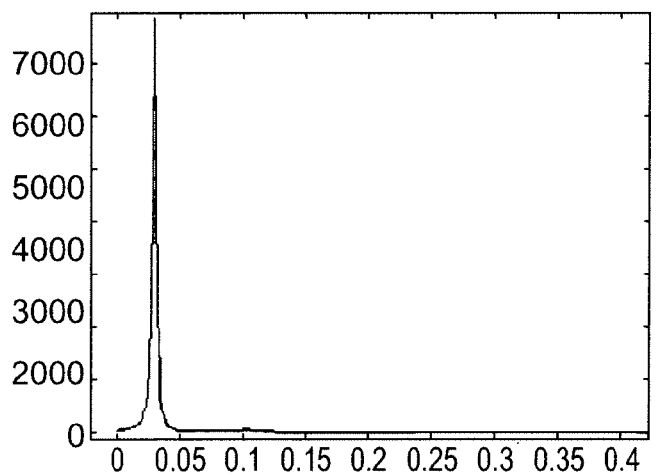

Preferred non-transform, frequency-domain methods include implementations of auto-regression techniques. Auto-regression based methods are advantageous for respiratory data series that are of relatively short duration or that have relatively fewer individual samples. Also, auto-regression based methods are advantageous for shorter the window length in comparison to transform methods. These techniques also can process irregularly sampled data and therefore do not require resampling of breath-by-breath data. Their disadvantage is that shorter window lengths or data series necessarily lead to decreased frequency resolution that may cause finer details to be missed. FIG. 2E illustrates spectral estimates provided by an auto-regression technique known as the Burg method (using order estimation according to information criterion due to Akaike) (both as known in the art) applied to a VE signal. It can be appreciated that the fundamental PB frequency is identified with an accuracy comparable to that of FIG. 2B. However, the small peak at about 0.06 Hz is almost smeared. Again, the presence or absence of PB can be ascertained from the auto-regression applied to VE signals by the presence or absence of a spectral power limited to a relatively small frequency band about a principal frequency that is likely to be a PB frequency. Therefore, where applicable, Lomb-Scargle method and similar methods are preferred where applicable for VE data, otherwise an auto-regression can be used.

Further preferred frequency domain methods are useful for analysis of primary respiratory signals which reflect moment-by-moment respiratory activities. Examples of such primary signals, in preferred embodiments, include signals returned by respiratory sensors that reflect the moment-by-moment rib cage (RC) and/or abdominal (AB) sizes which vary due to respiratory activities. Further examples include moment-by-moment lung volumes (referred to as a tidal volume (Vt) signal), which can be determined by combining RC and AB signals. Sequences of breath-by-breath Vt and VE signals can be derived from these primary signals.

Primary signals represent both changes due to individual breaths as well as changes due to waxing and waning of overall respiration. Accordingly, spectral analysis of primary signals includes spectral energy components at the respiratory frequency and components at the rate of overall changes. In the healthy subject, PB is absent and overall respiration is changes little (absent changes in exertion and so forth), so primary signals typically have spectral energy components only at respiratory frequencies, which are typically <0.1 Hz. If PB is present in a subject, primary signals typically have spectral energy components at both the respiratory frequency and at the PB (envelope) frequency. Such subjects typically have a higher base respiration rate so that the respiratory frequency components are now usually >0.2 Hz. PB frequency components typically are at lower frequencies, typically <0.1 Hz.

Figure 2F:
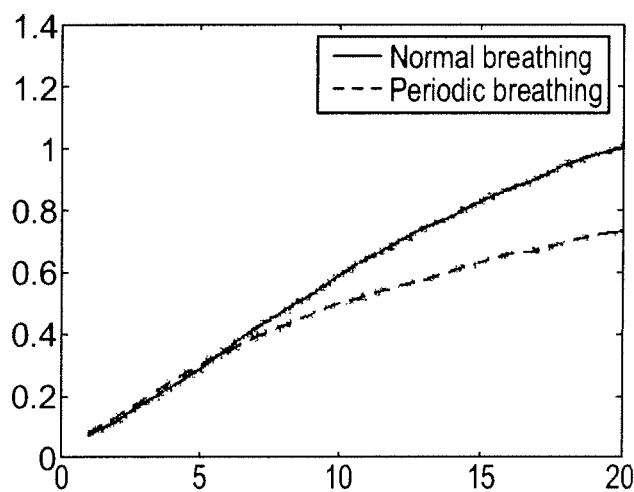
Figure 3A:
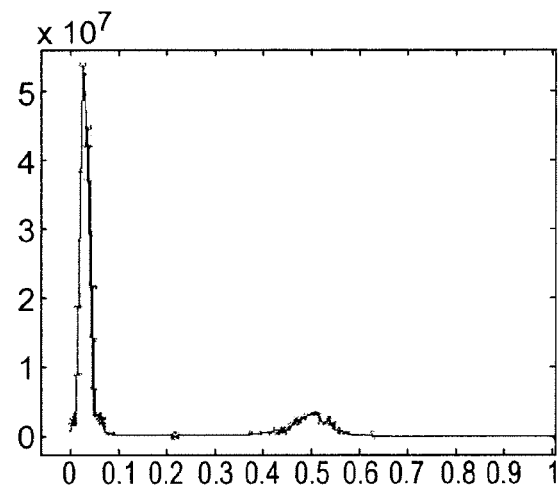
FIG. 3A-E illustrate results of additional periodic breathing methods of this invention.
Figure 3B:
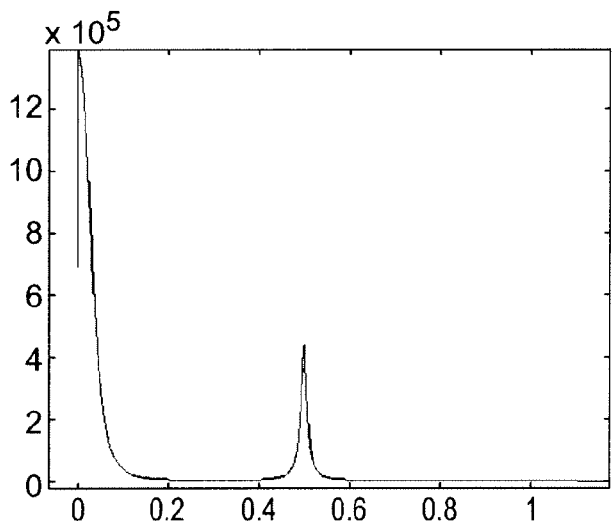

FIG. 3A-E illustrate spectra of primary Vt signals sampled at approximately 50 Hz. (These input signals are different from the input analyzed in FIGS. 2A-F, and the spectra do not necessarily match.) In FIGS. 3A-E, the vertical scale is spectral power and the horizontal scale is frequency in Hertz. FIGS. 3A and 3B illustrate a subject with periodic breathing analyzed according to the above-described Welch periodogram method and the auto-regression method, respectively, applied to a ten minute sample of primary Vt signals. Clearly visible in both figures are two spectral-power peaks. The first peak at approximately 0.05 Hz represents the PB envelope frequency (or PB frequency). The second peak at approximately 0.5 Hz representing represents the underlying frequency of individual breaths (the respiratory rate or frequency).

Preferred frequency-domain methods directed to analyzing primary respiratory sensor data utilize a method referred to as signal "rectification". Rectification is advantageous because it can both enhance actual frequency components present in the respiratory signal while limiting spurious frequency components representing artifact. To rectify a sampled signal, the signal is first de-trended by removing the local mean value of the input signal, and the absolute value of the de-trended input signal is found. Next, the absolute value signal is spectrally analyzed by, e.g., any of the above-described methods, for example, by the auto-regression method or by the Welch periodogram method. See e.g., Myers et al., 2003, *Rectification and non-linear pre-processing of EMG signals for cortico-muscular analysis*, J. Neurosci. Methods. April 15; 124(2):157-65.

Figure 3D:
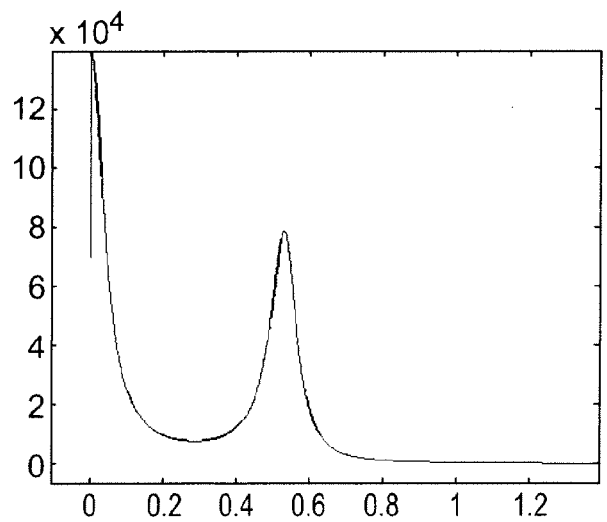

FIG. 3D compared with FIGS. 3A-B illustrate how rectification enhances actual frequency components present in the input primary Vt signal. FIG. 3D illustrates the auto-regression spectrum of the rectified input signal already illustrated in FIGS. 3A-B. It is apparent that both frequency components are clear and distinct and that the second peak at approximately 0.5 Hz (representing the respiration frequency) is enhanced relative to the first peak at approximately 0.05 Hz (representing the waxing and waning of PB). Thus, by rectifying the input signal, the presence of two actual frequency components in the input signal, and therefore the presence of PB, can therefore be more readily and more reliably recognized.

Figure 3C:
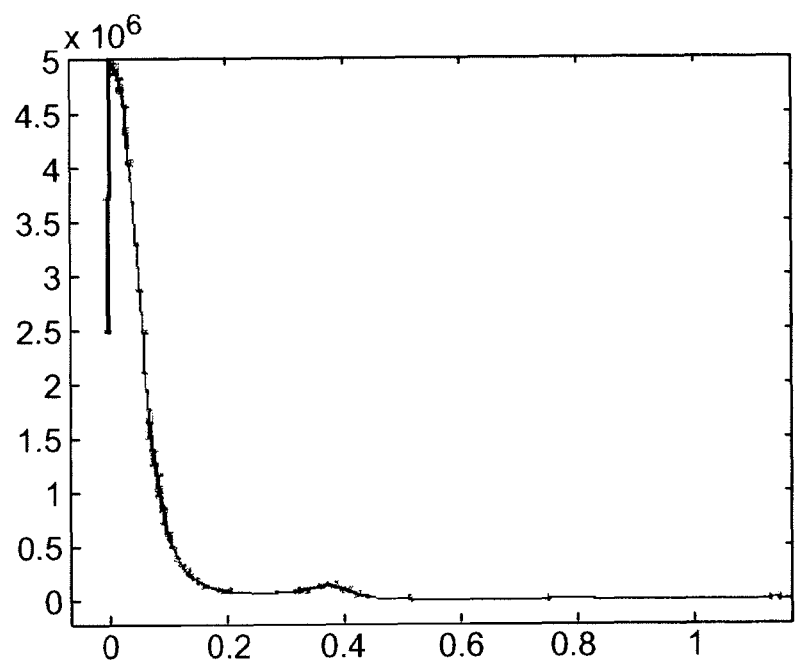
Figure 3E:
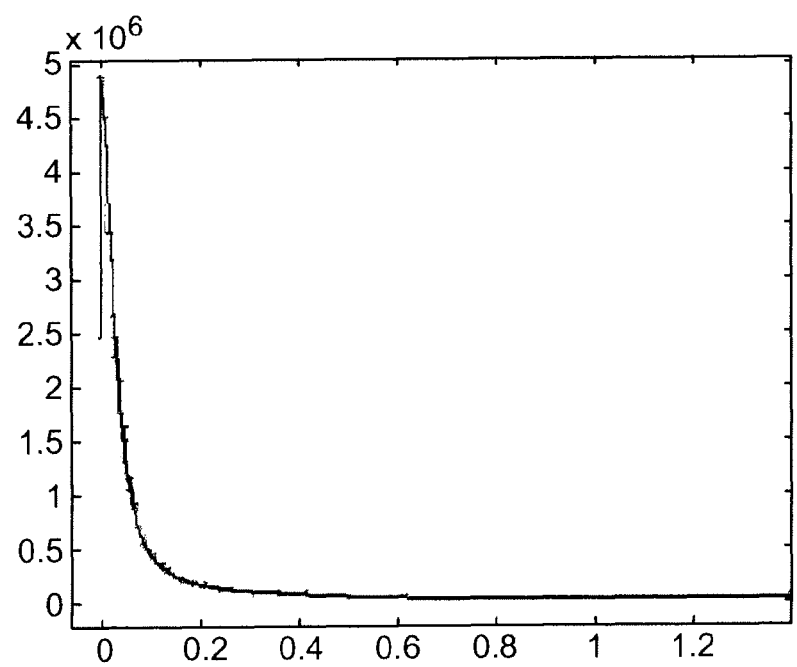

FIG. 3C compared with FIG. 3E illustrates how rectification limits spurious frequency components present in the input primary Vt signal. FIG. 3C illustrates the auto-regression spectrum of normal breathing without any PB components. And even in the absence of PB, a low amplitude secondary peak is present at about 0.4 Hz is present in FIG. 3C. The presence of two peaks could be incorrectly interpreted as indicated the presence of PB. FIG. 3E illustrates the auto-regression spectrum of the rectified normal breathing (no PB) signal. It is seen that the possibly-confusing secondary component present in FIG. 3C at about 0.4 Hz is absent in FIG. 3E. Thus, by rectifying the input signal, the presence of only one actual frequency component in the input signal, and therefore the absence of PB, can therefore be more readily and more reliably recognized.

In summary, rectification of the input signal makes the presence or absence of two actual and valid peaks more readily and reliably recognized. Spectral power peaks can be recognized by various known techniques such as thresholding. If PB is present, there must be 2 valid peaks; if there is only one valid peak, then PB is absent. It should be noted that rectification will distort frequencies slightly, especially lower frequencies. Therefore, once PB has been established to be present, the non-rectified input signal should spectrally analyzed to better determine actual frequencies without distortion.

Among the non-linear analysis techniques, methods based on entropy are preferred. It is well known that entropy is a measure of structure present in data. Data with higher the entropy has more disorder, less structure, and less predictability (but greater information content), while data streams with lower entropy have more order, more structure, and less predictability (but lower information content).

Comparing normal respiration and PB, it is expected that PB is more structured, less disordered, and more predictable than normal breathing. Normal breathing consists of a sequence of similar breaths space apart by an interval that randomly varies in a small range about an average breath-breath interval. PB, on the other hand, includes additional order, namely that the breath amplitude regularly vary at the PB frequency. This has been discussed above in view of frequency domain data. Therefore, it can be expected that the presence or absence of PB in a window of breath data can be estimated from its entropy. And the occurrence of PB over time can be estimated from the entropy of successive windows of respiratory data.

However, a single entropy value may not adequately reflect the order present in PB data. At the scale of the breath rate, the order in both normal breathing and PB are similarly dominated by the random variation of breath-breath interval about their average. It is only at the longer scale of the PB frequency that PB appear more orderly than normal breathing. Therefore, at a short scale, PB and normal breathing can be expected to have similar entropies. But at longer scales, PB can be expected to have less entropy than normal breathing. Therefore, it can be further expected that the presence or absence of PB in a window of breath data can be better estimated from entropy at two of more scales.

For these reasons, preferred non-linear, time-domain methods determine two or more entropies sensitive to different scales in the data. One preferred method is referred to as multi-scale entropy. In exemplary implementations, multi-scale methods first determine the entropy of the input data time series. Then, from the input data time series, they construct one or more derivative time series that are increasingly coarsely grained in time and determine their entropies. The entropies of the input data time series and of the more coarsely grained derivative data time series are taken to represent the relative order or structure present in the input data series at scales from the scale of the input data series to the longer scales of the derivative data series.

Many techniques known for coarsely-graining a data series are suitable in this invention. In exemplary preferred embodiments, an original time series is coarse grained by dividing the original data series into a sequence of non-overlapping blocks, each block having the same number, T, of data points from the original series, and then, by combining the data values in each block into a single value representative of that block. The resulting derivative data series is shorter than the original, having data points only for the sequential blocks of the original data series, and is taken to represent a scale T times larger than the scale of the original data series. Data values in a block can be combined by, e.g., averaging. according to the following equation:

$$v_j^T = \frac{1}{T} \sum_{i=(j-1)T+1}^{jT} w_i \quad 1 \le j \le N/T$$

Here, $x_i$ are the N input data values of the original data series; these are divided into a sequence of M blocks, M=N/T, each block having T input data points; the data points in the j'th block averaged to form representative value $v_j^T$; and $v_j^T$ $1<=j<=T$ are the output values of the derivative series. The derivative data series is considered to have a scale T times the scale of the input data series. See, e.g., Costa et al., 2002, Multiscale analysis of complex physiological time series, *Phys. Rev. Lett.* 89(6). Data values can also be combined according to other statistical techniques for constructing representative values. Also, data blocks can be partially overlapping. Instead of analyzing data time series, multiscale entropy can also be applied to the transform coefficients of time series.

There are many known methods for computing the entropies of the input data series and of the derivative data series in the multiscale method. These methods include simple entropy, Kolmogorov-Sinai (KS) entropy, Eckmann-Ruelle (ER) entropy, Fourier entropy, Wavelet entropy, Renyi entropy, Lyapunov spectra, Hausdorff dimension, correlation dimension etc. See, e.g., Pincus, 1991, Approximate entropy as a measure of system complexity, Proc. Natl. Acad. Sci. USA 88:2297-2301. Simple entropy at scale T, $H^T$, is determined according to the formula:

$$H^T = \sum_i p(v_i^T) \log(p(v_i^T))$$

where $p(v_j^T)$ is the probability of occurrence of value $v_j^T$ in the data set (e.g., a normalized histogram of the data set. Although readily determined, simple entropy is less preferred because it is easily distorted by noise and artifact in the input data series. The KS entropy is a useful parameter to characterize the dynamics of a system and represents the mean rate of creation of information. Similar to this, but computationally easier, is the approximate entropy (ApEn), which is essentially an estimate of KS entropy on a finite duration series. Heuristically, E-R entropy and ApEn measure the (logarithmic) likelihood that runs of patterns that are close remain close on the next incremental comparisons.

The preferred entropy is known as sample entropy (SampEn), and is a modification of the approximate entropy that corrects certain bias (due to including self-matches) present in approximate entropy. See, e.g., Richman et al., 2000, *Physiological time-series analysis using approximate entropy and sample entropy*, Am. J. Physiol. Heart Circ. Physiol. 278: H2039-H2049. Sample entropy is more readily calculated and is less dependent on the length of the time-series. Briefly, this entropy is the negative natural logarithm of an estimate of the conditional probability that two or more sub-series (epochs) of length m, which are selected from the input data series beginning at different data points of the input data series and which match pointwise within a tolerance r, also match at the next (m+1'st) data point. Alternatively, other entropies could be used in the multiscale method.

In more detail, the sample entropy method constructs consecutive runs (groups) of successive signal points all of which match each other within a specified tolerance, r. The method finds consecutive groups of matches (runs) by finding all points that match a first signal point within the tolerance, r. The signal points that first match begin runs of initial length 1, and the signal points that don't match begin runs of initial length 0. If those signal points following runs of length 1 also match the second point, the runs are now of length 2; otherwise, the run is ended. If those signal points following runs of length 0 match the second point, the runs are now of length 1. This procedure of finding runs is continued until the end of the data.

Next, the length of template matches are recorded in counters A(k) and B(k) for all group lengths, k, up to maximum length, m. (When a run ends at the last point in the data, the A(k) counters are incremented but the B(k) counters are not.) Once all template matches have been recorded, sample entropy values are calculated according to the equation:

SampEn(k,r,N)=−ln(A(k)/B(k−1)

for k=0, 1, . . . , m−1 with B(0)=N, the length of the input series.

The preferred multi-scale entropy method then computes the sample entropies (multiscale sample entropy) of the input data series and of the derivative, more coarsely-grained data series, which entropies are the entropies at the different time scales. Preferred parameters are: the tolerance r is preferably approximately 20% of the standard deviation of the input data series; and the length m is set to approximately 2.

However, the presence of outlier values in the input data series may distort multiscale sample entropy. Thus, it is preferred, before determining multiscale sample entropy, to first identify and delete outlier values from the input data series. In preferred embodiments, a data value is considered as outlier value if it differs from the mean of the input data series by more than approximately two standard deviations (of the input data series). Multiscale sample entropy with outlier rejection has been found to be more robust than those prior methods that identify outliers by searching for outlier values in the breath rate or volume data and then by interpolating respiratory and/or cardiac to remove only these identified outliers. These prior methods are limited because undesired artifacts often do not appear as outliers, and also because interpolation may introduce bias in certain respiratory measurements.

FIG. 2F illustrates the results of an exemplary multiscale entropy method applied to the same data as that processed in FIG. 1A. In FIG. 2F the vertical scale is sample entropy and the horizontal scale is entropy scale. Here, the horizontal scale represents entropy varying from 0 to 1, and the vertical scale represent the scale of the multiscale entropy method. The upper curve in the figure is the multiscale entropy for normal breathing, and the lower curve is the multiscale entropy from PB. It is apparent that, as expected, PB and normal breathing have similar entropies at shorter scales, so that entropy at these scales does not clearly differentiate between PB and normal breathing. However, at longer entropy scales, the entropy of PB is distinguishably less than the entropy of normal breathing. Also the entropy curve has a smaller slope. Therefore, multiscale entropy can differentiate normal breathing and PB.

For the cited analysis methods, see, e.g., Manolakis D. G. et al, 2005, *Statistical and Adaptive Signal Processing: Spectral Estimation, Signal Modeling, Adaptive Filtering and Array Processing*, Artech House Signal Processing Library; and Brillinger D R, 1981 2nd ed., *Time Series—Data Analysis and Theory*, Holden Day, San Francisco. See, also, Press et. al, 1992, *Numerical Recipes in C*, Cambridge University Press.

Analysis of Heart Rate Variability (HRV)

This invention provides methods for more reliable and accurate determination of HRV by recognizing and eliminating irregularities in input data that would otherwise distort the HRV determination. By way of introduction, HRV determination and known methods for recognizing input data irregularities are briefly described. First, standard methods are known for HRV determination, both by time-domain analysis and by frequency-domain analysis of cardiac rate data. See, e.g., Camm et al., 1996, (cited above). Input cardiac rate data is usually determined as the time intervals between successive R waves (R-R intervals) in a concurrent electrocardiogram (ECG) record. R wave occurrences are readily recognized in the ECG by known methods, and R-R intervals are then the sequence of time intervals between successive R wave occurrences. Irregularities in the input RR-interval data can seriously distort HRV, and particular care is needed in selecting "clean" data sufficiently free of such irregularities. Different "cleaning" methods have been applied in cases of different types of irregularities.

RR interval irregularities known to arise from non-cardiac causes, such as motion and other artifacts arising especially in ambulatory monitoring. Therefore, HRV determination can be limited to periods when the subject is not moving as determined from, e.g., concurrent accelerometer data. Alternatively, HRV is determined during subject motion but using data that has been filtered to limit or remove recognized motion artifacts. Methods for limiting motion artifacts are known. See, e.g., U.S. patent application Ser. No. 10/991,877 filed Nov. 18, 2004, which is incorporated herein by reference herein in its entirety.

RR interval irregularities known to arise from intrinsic cardiac causes, such as arrhythmias. A confounding arrhythmia is known as ectopic ventricular beats or ventricular premature beats (VPB). Because, VPBs are more or less spontaneous ventricular contractions occurring during an otherwise normal diastole, they can distort a portion of R-R interval data following the VPB. Again, HRV determination can be limited to data free of VPBs occurrences, or can be performed with data that has been filtered and corrected to correct for any VPBs that did occur. Such correction methods are known in the art and are advantageously employed in this invention. See, e.g., Lippman et al., 1994, *Comparison of methods for removal of ectopy in measurement of heart rate variability*, Am J. Physiol. 1994 July; 267(1 Pt 2):H411-8.

RR interval irregularities also arise from breathing irregularities. Cardiac rate is known to very during breathing (e.g., respiratory sinus arrhythmia), and breathing irregularities can thereby lead to RR interval irregularities. For example, breathing irregularities can arise from intrinsic respiratory process such as speaking, coughing, sighing, sneezing, and so forth. Methods are known for recognizing these respiratory events. See, e.g., U.S. patent application Ser. Nos. 10/822,260 filed Apr. 9, 2004; and 10/991,877 filed Nov. 18, 2004, both of which are incorporated herein by reference herein in their entireties. Similarly, PB can cause low frequency (e.g. the PB frequency) cardiac rate variations. The methods of this invention can recognize PB, so that periods with PB can be excluded from HRV determination. Optionally, HRV can be determined from RR interval data from a period during which PB was occurring and then optionally corrected for PB-induced variations.

However, the inventors have found further classes of breathing irregularities, perhaps not heretofore appreciated, that the just-described methods are incapable of recognizing, and have provided methods for recognizing these further classes of breathing irregularities. The just-described methods generally search for irregularities in respiratory data, such as tidal volumes (Vt) or breath rates (RR), that have previously been derived from raw respiratory sensor data. The methods provided here, instead, examine raw signals as directly received from respiratory sensors. The provided methods are particularly advantageous for respiratory monitoring systems with respiratory sensors that are directly sensitive to time varying volumes, areas, sizes, circumferences, lengths, and the like of portions, of a subject's thorax. Respiratory inductive plethysmographic ("respiratory IP" or "RIP") is a preferred monitoring system of this type. RIP sensors are often configured to be directly sensitive to the time-varying size of a subject's rib cage (RC), or to the time-varying size of a subject's (AB), or to the size of both the RC and the AB. When applied to RIP systems, the provided methods preferably examine the raw RC signals and/or the raw AB signals.

The provided methods search the raw respiratory sensor signals for unusual variability that reflect breathing irregularities that can lead to RR interval irregularities. In detail, the provided methods search input sensor data to identify the position and values of signal peaks or maxima (occurring at end inspiration) and signal troughs or minima (occurring at begin inspiration). During stable breathing without artifacts, it has been found that there is no significant variation between either successive signal maxima or successive signal minima. It has been found that significant changes in the sensor signal minima or sensor signal maxima are associated with various irregularities and artifacts. For example, sensor signal baseline commonly shifts during postural changes or sudden activity, and that these baseline changes change the values of signal maxima or minima. Significant breath-by-breath changes in signal maxima or minima commonly accompany continuous activity, speech, coughs, and so forth. However, certain respiratory events have been found to be commonly associated with significant changes only in signal maxima or only in signal minima. For example, sighs or apneas have been found to lead to changes in signal maxima only. Therefore, in many situations, stable signal minimum are sufficient for a determination of stable breathing.

Unusual signal variability is determined by comparing recent or current sensor signal input in a current window with sensor signal input received during a preceding period or window. In a preferred embodiment, significant changes in signal maxima or minima are determined finding values representative of signal maxima and minima observed during a preceding window, and then by thresholding the differences in the current window's sensor signal maxima or minima from the representative values. Finding representative values and thresholding are preferably performed data window by data window. An exemplary thresholding method using the following formulas:

$$V_{peak} = \prod_{j=1}^{N}\left[\frac{\|EI_j - \widehat{EI}\|}{\widehat{VI}} > V_{thresh}\right]$$

and $$V_{trough} = \prod_{j=1}^{N}\left[\frac{\|BI_j - \widehat{BI}\|}{\widehat{VI}} > V_{thresh}\right]$$

and $$V_r = \begin{cases} V_{peak} \wedge V_{trough} \\ V_{trough} \end{cases}$$

Here, $V_{peak}$ ($V_{trough}$) are Boolean variables that are set to False according to the above equation if there is a significant change in any signal maxima (minima) in the current window from the representative value. N is the number of breaths in the current window, $\widehat{EI}$ is representative of N signal maxima; $\widehat{BI}$ is representative of the N signal minima; $\widehat{VI}$ is representative of the N tidal volumes (end inspiration volume minus the previous end expiration volume). In this exemplary implementation, representative value are determined as medians. Further, $BI_j$ is the value of the j'th minima; and $EI_j$ is the value of the j'th maxima. $V_{thresh}$ is a selected threshold above which differences between current values and representative values (as normalized by the representative values for the tidal volume) are considered significant (alternatively, different thresholds can be selected for signal maxima and minima). $V_{peak}$ and $V_{trough}$ are Boolean valued computed according to the above equation. $V_r$ is a Boolean variable set to True when stable breathing is detected. In alternative embodiments, $V_r$ is True when stable troughs are detected, or when stable troughs and peaks are detected.

In alternative implementations, representative values can be chosen by other statistical techniques, e.g., averages. Also, $V_{peak}$ ($V_{trough}$) can depend on the differences of successive signal maxima (minima), and threshold used for evaluating peaks and troughs may be different. For example, $$V_{peak} = \prod_{j=2}^{N}\left[\frac{\|EI_j - EI_{j-1}\|}{\widehat{VI}} > V_{thresh}^{peak}\right]$$

and $$V_{trough} = \prod_{j=2}^{N}\left[\frac{\|BI_j - BI_{j-1}\|}{\widehat{VI}} > V_{thresh}^{trough}\right]$$

Other related methods for determining $V_{peak}$ and $V_{trough}$ will be apparent and are within the scope of this invention. Also the Boolean threshold test can be replaced by other test schemes. For example, $V_{peak}$ ($V_{trough}$) can be set to False only if a certain fraction of the maxima (minima) exceed the threshold.

This provided methods are preferably performed data window by data window, each window many be from several seconds to many minutes. If a particular window on first examination contains only one or two unstable breaths, this window can be shortened so as to exclude the unstable breaths and the shortened window can be checked again for additional unstable breaths. If no additional unstable breaths are found, HRV analysis can then be performed on the shortened window, correcting for changes in window duration. Alternatively, especially where short windows are used, the entire window can be rejected if any unstable breaths are found.

Figure 4A:
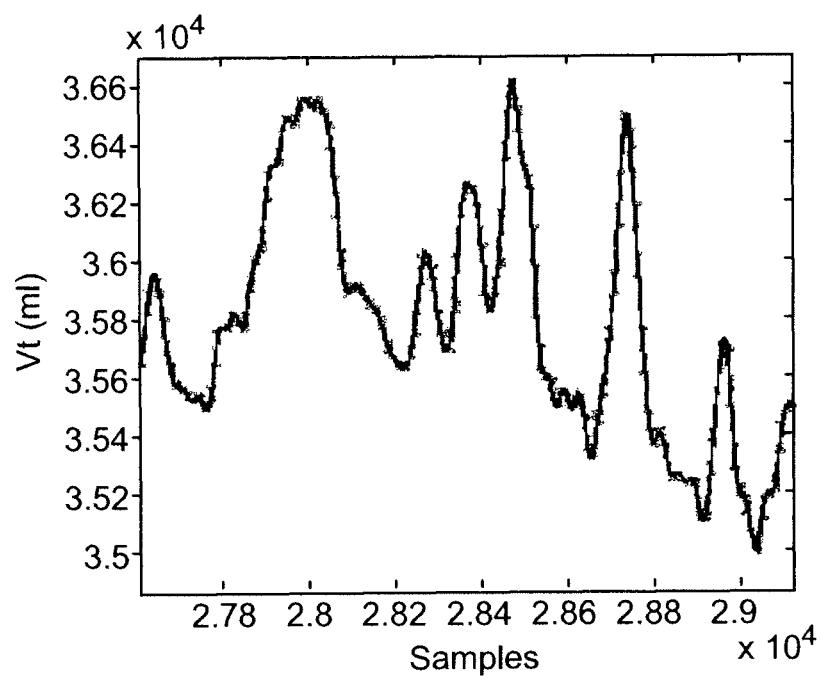
FIG. 4A-C illustrate lung volume data with and without artifacts.
Figure 4B:
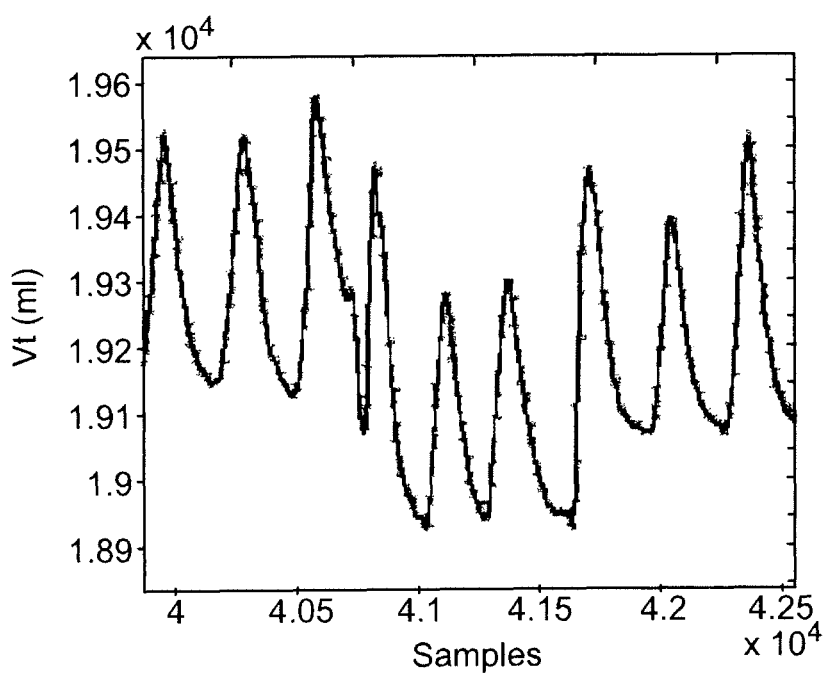
Figure 4C:
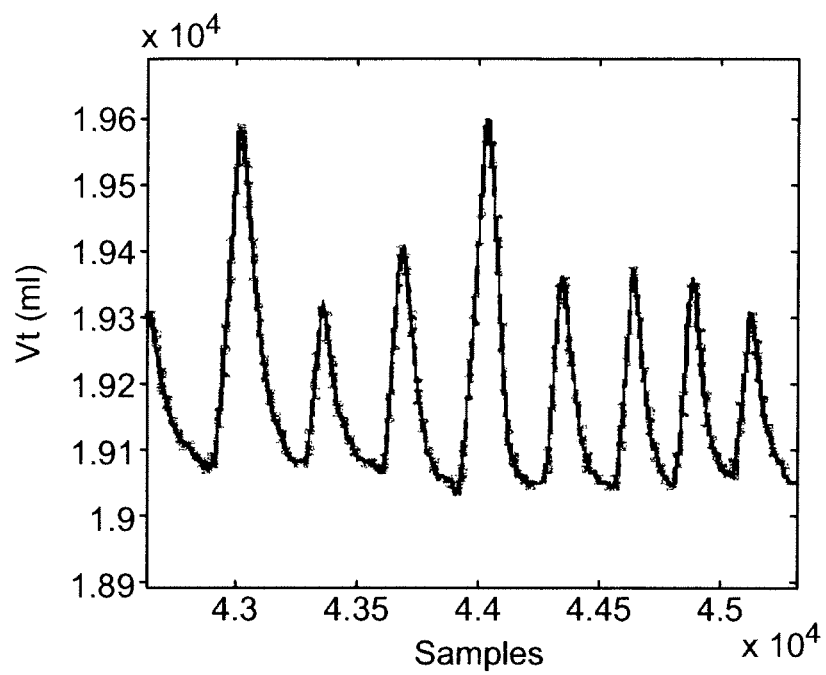

FIGS. 4A-C are examples of the above-described method. For these example, N=10 and Vthresh=0.2 have been chosen as suitable parameters. First, FIG. 4A illustrates a period of irregular breathing during which neither the peaks nor the troughs are stable. Consequently, the tidal volumes, the distance from the peaks to their succeeding troughs, are widely varying. Both alternative embodiments will determine that such a breathing pattern is not stable and optionally exclude it from HRV analysis.

Next, FIG. 4B illustrates more regular breathing in which, although the tidal volumes are substantially stable, both the peaks and the troughs are briefly (for a few breaths) substantially below their recent baseline. It should be noted that this brief instability was associated with a shift in posture so slight as to not be detected by a concurrent accelerometer that records the subject's accelerations due to posture and activity. Both alternative embodiments will again determine that such a breathing pattern is not stable and optionally exclude it from HRV analysis. The above described prior methods will probably not detect this irregularity.

Lastly, FIG. 4C illustrates a further example of more regular breathing. Here, the troughs remains stable near their recent baseline. However, the peaks, and consequently the tidal volumes, are widely varying from baseline. The first alternative embodiment determines that such a breathing pattern is not stable because it requires that both the peaks and the troughs be stable. In contrast, the second alternative embodiment determines that such a breathing pattern is stable because it requires that only the troughs be stable.

Analysis of Additional Inputs

Thoraco-cardiography (TCG) non-invasively provides indicia of cardiac output (CO) from moment-by-moment measurements of the anterior chest size. Cardiac pulsations, which reflect cardiac diastoles and systoles, can affect the size (e.g., the length of a transverse segment at the level of the xiphoid process) of the overlying anterior chest. Although respiration dominates changes in anterior chest size, cardiac activity and cardiac pulsations change anterior chest size albeit with an amplitude much less than that of inhalation and exhalation. Filtering and averaging techniques (e.g., ensemble averaging) have been developed to extract clearly cardiac activity from the larger respiratory activity. See, e.g., U.S. Pat. Nos. 5,178,151 issued 1993 and 6,783,498 issued 2004; and U.S. application Ser. No. 10/991,877 filed Nov. 18, 2004, all of which are incorporated herein by reference herein in their entireties. These techniques provide indices of cardiac output that reflect (or are monotonically related to, or approximately proportional to) actual cardiac output data measured by standard and invasive techniques.

CO is an important parameter defining CHF. Acute changes in TCG output data in the absence of other signs can alone indicate decompensation, and in the presence of other above-described signs, can confirm decompensation. It is possible that chronic changes in TCG output data can indicate the progress of a subject's CHF.

Other advantageous inputs include data from one to three axis accelerometers; blood oxygen saturation (spO2) data from pulse oximeters; subject temperature, and the like. Acceleration data can be processed as known in the art to provide indicia of the subject's posture and activity level. Pulse oximeters are often include a processing module that directly outputs spO2 information.

Posture, activity, and spO2 provide useful references for the cardio-respiratory signs concurrently recognized by above-described signs. For example, apparent CHF decompensation occurring only during exercise is of less concern the apparent CHF decompensation occurring intermittently at rest.

Preferred System Implementations

The monitoring data input to and analyzed by the above-described methods of this invention can be gathered by a wide variety of monitoring systems, e.g., systems designed for in-hospital use, or for in-clinic use, or for ambulatory use, or for use in other environments. Preferred embodiments of this invention are directed to ambulatory monitoring where monitoring data is gathered while subject's perform their normal daily activities in a substantially unrestrained manner. Also, the methods of this invention can implemented on a wide-range of computer systems, from handheld-type systems to server-type systems. Preferred embodiments of this invention implement the methods of this invention on an portable processing device that can readily be carried by an ambulatory subject. In such preferred embodiments, a subject's CHF status can be immediately available to the subject, and can also be remotely transmitted to caregivers for later review.

An example of the preferred embodiments includes a garment (generally, any comfortable, unobtrusive wearable item) having incorporated physiological sensors, and an easily-carried processing device. When the garment is worn by a subject, the sensors return signals to the accompanying processing device; the processing device converts sensor signals into respiratory, cardiac, and other physiological parameters. This processing device (or another similar processing device) then performs the methods of this invention, which extract information describing the status of the wearer's CHF from the physiological parameters. CHF status and other monitoring information can be made available or displayed to the wearer in real time, or transferred or transmitted for off-line review by caregivers and others.

In more detail, suitable wearable items can include garments, jackets, bands, patches, and the like, made from a variety of materials, particularly elastic materials to insure a snug fit; they can be donned in one piece or include zippers, Velcro, snaps, and the like, that are joined after donning. Sensors can be incorporated into garments in many ways, for example, by weaving, or knitting, or braiding into a garment's fabric; or by being sewn or carried on, or mounted in, or attached to the garment; also flexible sensors can be glued, printed, sprayed and so forth onto inner or outer garment surfaces. See, e.g., U.S. Pat. No. 6,551,252.

The incorporated sensors preferable include respiratory IP sensors. Briefly, IP sensors comprise specially-configured conductive elements having inductances varying with their sizes. An IP sensor is included in an oscillator circuit so that it oscillates at a frequency varying with the IP sensor size. The oscillator frequency is then converted into digital data representing the size of the IP sensor. See, e.g., U.S. Pat. No. 6,551,252. IP sensor sensitive to RC and AB size can be calibrated and combined into a tidal volume (Vt) that accurately reflects the results of comparable clinical measurements. See, e.g., Sackner, M. A., 1996, A simple and reliable method to calibrate respiratory magnetometers and Respitrace, *J. Appl. Physiol.* 81:516-7; and Tabachnik et al., 1981, Measurement of ventilation in children using the respiratory inductive plethysmograph, *J. Pediatrics* 99:895-9. IP sensors at the anterior chest at the level of the xiphoid process on the anterior chest provide signals that can be processed to extract cardiac pulsation signal and indexes of CO. Wearable items can also incorporate accelerometers, pulse oximeters, and other sensors.

Figure 5:
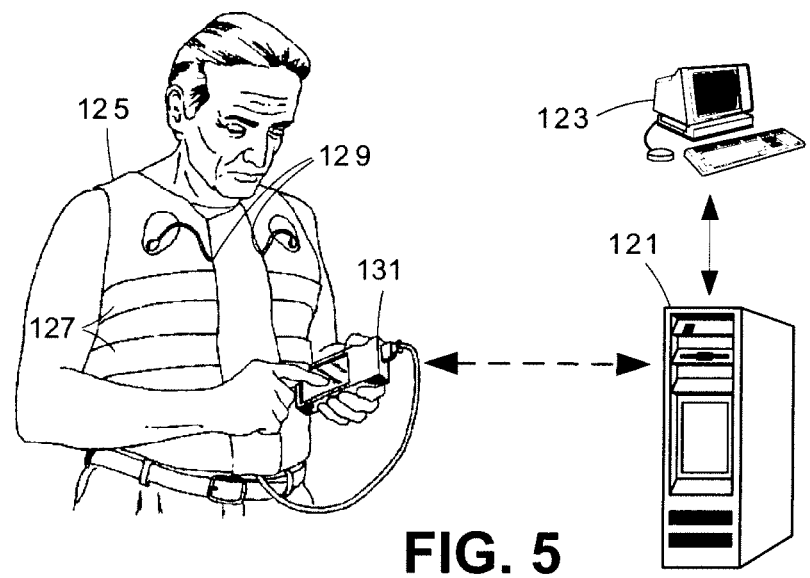
FIG. 5 illustrates an ambulatory monitoring system.

FIG. 5 illustrates an exemplary ambulatory implementation of this invention. A subject is shown wearing a garment-like item 125 that incorporates IP sensors 127 arranged at the RC and AB and ECG electrodes 129. The garment may incorporate other sensors. Associated processing device 131 is easily carried by the subject, and receives and processes sensor signals, performs the methods of this invention, and displays results and data to the subject. Device 131 can also transmit sensor signals and data to remote systems 121 by, e.g., wireless transmission or by physical transport. The remote systems include user interface devices 123 at which caregivers can review data in real time or at a later time.

Figure 6:
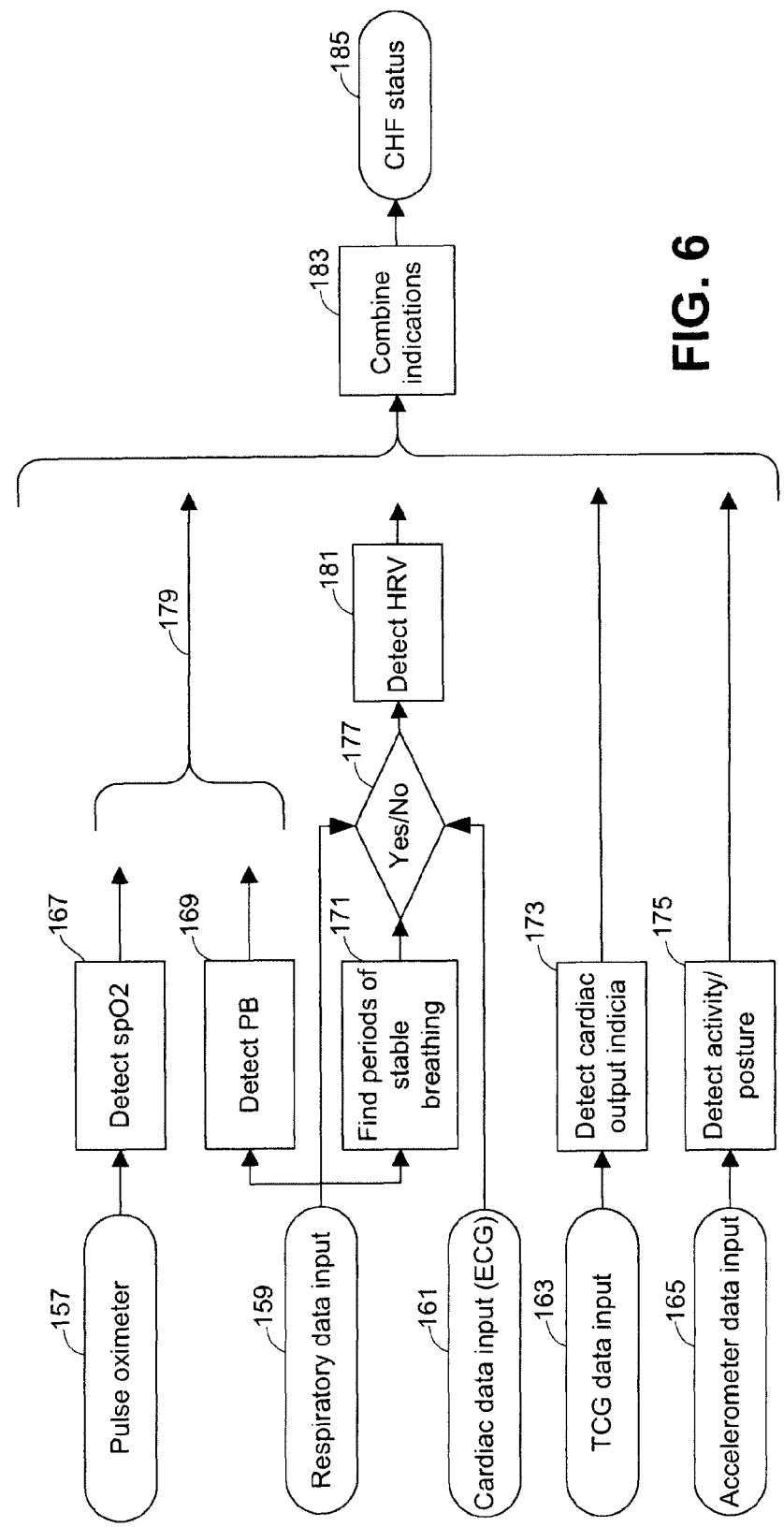
FIG. 6 illustrates an exemplary system employing the techniques of this invention in order to determine CHF status.

In preferred ambulatory embodiments, two or more of the methods of this invention are brought together so that their individual indications concerning subject CHF status can pooled. FIG. 6 illustrates an exemplary system embodiment in which all methods are brought together in order to processes data from the multiple data sources 157, 159, 161, 163, and 165 (assumed to be concurrently available). Pulse oximeter data 157 is converted 167 into an spO2 value by, e.g., methods that are part of the pulse oximeter itself. Indices of cardiac output, e.g., liters of blood pumped per minute, are extracted 173 from TCG data 163. Indices of posture and activity are extracted 175 from accelerometer data 165. These three types of data are generally used as a context in which to assess the cardiac and respiratory indices.

Respiratory data 159 has multiple uses. First, respiratory data 159 it is processed 169 alone in order to detect the presence of PB. Joint indications 179 are formed from the PB and spO2 results, because it is known that the concurrent presence of PB and of a normal spO2 is more significant than PB with a reduced spO2. Alternatively, both data items are considered individually. Next respiratory data 159 and cardiac (ECG) data 161 are jointly processed in order to properly detect 181 HRV. Respiratory data is first processed 171 to determine periods of stable breathing. If breathing is not currently stable, HRV processing is blocked 177. If breathing is currently stable, HRV processing proceeds 177 and is completed in step 181.

The five items bearing on subject CHF status—spO2, PB, HRV, cardiac output, and posture and activity—can be optionally but preferably combined 183 into a summary CHF status. The five indications can be also output individually. These items and indications can be combined by known medical decision methods. For example, rules can encode the medical evaluation processes for these indications. Weights can optionally be attached to rules so that a degree of likelihood of the evaluation results can be determined. Alternatively, current indications and their values, e.g., the period and amplitude of PB, can be combined according to a discriminant function into a single estimation of CHF status. This estimation can be thresholded or otherwise converted into the statistically most likely CHF status. Bayesian methods can also be used.

Summary CHF status and/or the individual items and indications are output 185 to the subject and/or to caregivers.

This methods of this invention are performed on software or firmware programmable systems. In the case of software programming, methods are coded in standard computer languages, such as C, C++, or in high level application languages, such as Matlab and associated toolboxes (Math Works, Natick, Mass.). Code is then translated or compiled into executable computer instructions for controlling a microprocessor or similar. In the case of firmware programming, higher level method specifications written in software languages or hardware languages such as VHDL, are generally translated into bit codes by tools supplied by the manufacturer of the hardware part that is being programmed. For example, manufacturer's tools prepare bit-streams for configuring FPGAs. The invention also includes software distributions, e.g., on computer-readable media, having encoded the method of this invention for execution on a computer or for programming a firmware device.

A number of references are cited herein, including patents and patent applications, and their entire disclosures are incorporated herein, in their entirety, by reference for all purposes. Further, none of these references, regardless of how characterized above, is admitted as prior to the invention of the subject matter claimed herein.

The preferred embodiments described herein are not intended to limit the scope of the invention. Instead, this invention and its appended claims are intended to cover equivalent embodiments as well as modifications and configurations that will become apparent to those skilled in the art. Although specific features of the invention are shown in some drawings and not in others, this is for convenience only as each feature may be combined with any or all of the other features in accordance with the invention.

What is claimed is:

1. A method for automatically monitoring congestive heart failure (CHF) in a subject comprising:
   receiving signals, from a sensor, generated by non-invasively monitoring respiratory physiology of the subject, the signals conveying information concerning at least the subject's breath rate and volume;
   examining, with a processor, the received signals for determination of a minute ventilation (VE) signal and for indications of periodic breathing (PB), wherein the presence or absence of PB is determined through a multi-scale entropy analysis of the received signals and a power spectrum analysis of the VE signal;
   indicating the status of CHF in the subject to be of increased severity if indications of PB are found.

2. The method of claim 1 wherein the VE signal is sampled at a fixed sampling rate.

3. The method of claim 2 wherein the step of examining further comprises:
   forming an auto-correlogram by auto-correlating the VE signal at a zero temporal shift and at a plurality of non-zero temporal shifts; and
   examining the auto-correlogram for indications of PB, PB being indicated if the auto-correlogram comprises a significant maximum at a non-zero temporal shift adjacent to the central maximum at zero temporal shift.

4. The method of claim 2 wherein the power spectrum analysis comprises:
   forming a power spectrum by a Fourier transform method of the VE signal, the VE signal having been windowed; and
   examining the power spectrum for indications of PB, PB being indicated if the power spectrum comprises a significant maximum at a frequency characteristic of PB.

5. The method of claim 2 wherein the power spectrum analysis comprises:
   forming a power spectrum by a Lomb-Scargle method of the VE signal, the VE signal having been windowed; and
   examining the power spectrum for indications of PB, PB being indicated if the power spectrum comprises a significant maximum at a frequency characteristic of PB.

6. The method of claim 2 wherein the power spectrum analysis comprises:
   forming a power spectrum by a Burg method of the VE signal, the VE signal having been windowed; and
   examining the power spectrum for indications of PB, PB being indicated if the power spectrum comprises a significant maximum at a frequency characteristic of PB.

7. The method of claim 1 wherein the received signals convey information concerning the time-varying sizes of one or both of the subject's thorax (RC) and of the subject's abdomen (AB), and
   wherein the power spectrum analysis comprises forming a power spectrum of the received signals by one or more of an auto correlation method, a Fourier transform method, a Lomb-Scargle method, and a Burg method; and
   examining the power spectrum for indications of PB, PB being indicated if the power spectrum comprises two significant maxima, one at a frequency characteristic of PB and another at a frequency characteristic of respiration.

8. The method of claim 7 further comprising, prior to the step of forming a power spectrum, de-tending the received signals and rectifying the de-trended signals.

9. The method of claim 1 wherein the multi-scale entropy analysis further comprises:
   calculating a plurality of entropies of a plurality of additional signals, the plurality of additional signals being derived from the received signals by performing windowing followed by a plurality of degrees of coarse graining; and
   examining the plurality of entropies for indications of PB by comparing entropies at lesser degrees of coarse graining with entropies at greater degrees of coarse graining.

10. The method of claim 9 wherein one or more of the entropies are calculated according to the sample entropy method.

11. The method of claim 1, wherein examining the received signals further comprises examining the received signals for indications of reduced heart rate variability (HRV).

12. The method of claim 11, wherein indicating the status of CHF in the subject further comprises indicating the status of CHF in the subject in dependence on the indications of HRV.

13. The method of claim 1, wherein at least a portion of the signals are received when the subject is ambulatory.

14. The method of claim 12, wherein CHF is indicated to be of increased severity if indications of reduced HRV are found.

15. The method of claim 12, wherein the received signals also convey information concerning the magnitude of the subject's cardiac pulsations; wherein the received signals are examined for indications of cardiac output (CO), and wherein CHF is indicated to be of increased severity if indications of reduced CO are found.

16. The method of claim 12, wherein the received signals also convey information concerning the subject's blood oxygen content (spO2), and wherein CHF is indicated to be of increased severity if indications of reduced spO2 are found.

* * * * *